(12) United States Patent
Schmitz

(10) Patent No.: US 8,221,380 B2
(45) Date of Patent: Jul. 17, 2012

(54) METHOD FOR MANUFACTURING A THREE DIMENSIONALLY SHAPED ARTICLE COMPRISING HIP/THIGH PANELS AND A HOOP FROM A PLUS-SHAPED BLANK, AND SUCH AN ARTICLE

(76) Inventor: Christoph Schmitz, Euskirchen Stotzheim (DE)

( * ) Notice: Subject to any disclaimer, the term of this patent is extended or adjusted under 35 U.S.C. 154(b) by 539 days.

(21) Appl. No.: 12/442,636

(22) PCT Filed: Sep. 28, 2006

(86) PCT No.: PCT/EP2006/009430
§ 371 (c)(1),
(2), (4) Date: Mar. 24, 2009

(87) PCT Pub. No.: WO2008/037281
PCT Pub. Date: Apr. 3, 2008

(65) Prior Publication Data
US 2009/0275910 A1  Nov. 5, 2009

(51) Int. Cl.
*A61F 13/15* (2006.01)
*B32B 37/00* (2006.01)
(52) U.S. Cl. ............... 604/396; 604/385.28; 604/378; 156/256; 156/250; 156/264; 156/265; 156/263
(58) Field of Classification Search ........... 604/385.28, 604/378, 396; 156/256, 250, 264, 265, 263
See application file for complete search history.

(56) References Cited

U.S. PATENT DOCUMENTS

| 5,669,996 | A | 9/1997 | Jessup |
| 5,693,165 | A | 12/1997 | Schmitz |
| 2002/0084017 | A1 | 7/2002 | Rabe et al. |
| 2002/0103468 | A1 | 8/2002 | Nakakado et al. |

FOREIGN PATENT DOCUMENTS

| EP | 1393701 A | 3/2004 |
| WO | 2004103872 A | 12/2004 |

*Primary Examiner* — Jacqueline F. Stephens
(74) *Attorney, Agent, or Firm* — David A. Guerra

(57) ABSTRACT

The present invention relates to a method for the high production speed manufacturing of articles comprising a closed or hoop structure, such as garments like pants, or absorbent articles like diapers, having a waist- and leg hoops.

9 Claims, 24 Drawing Sheets

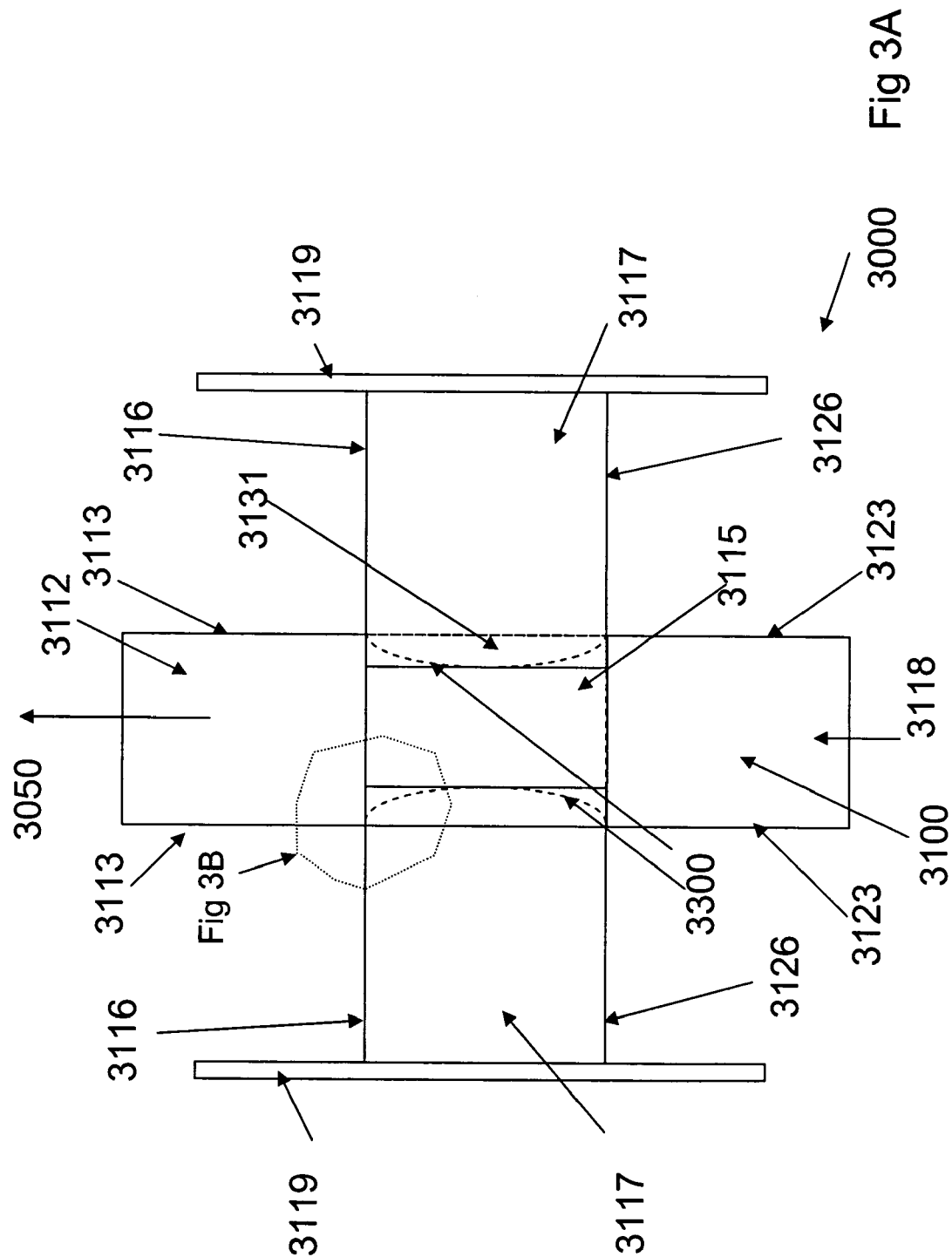

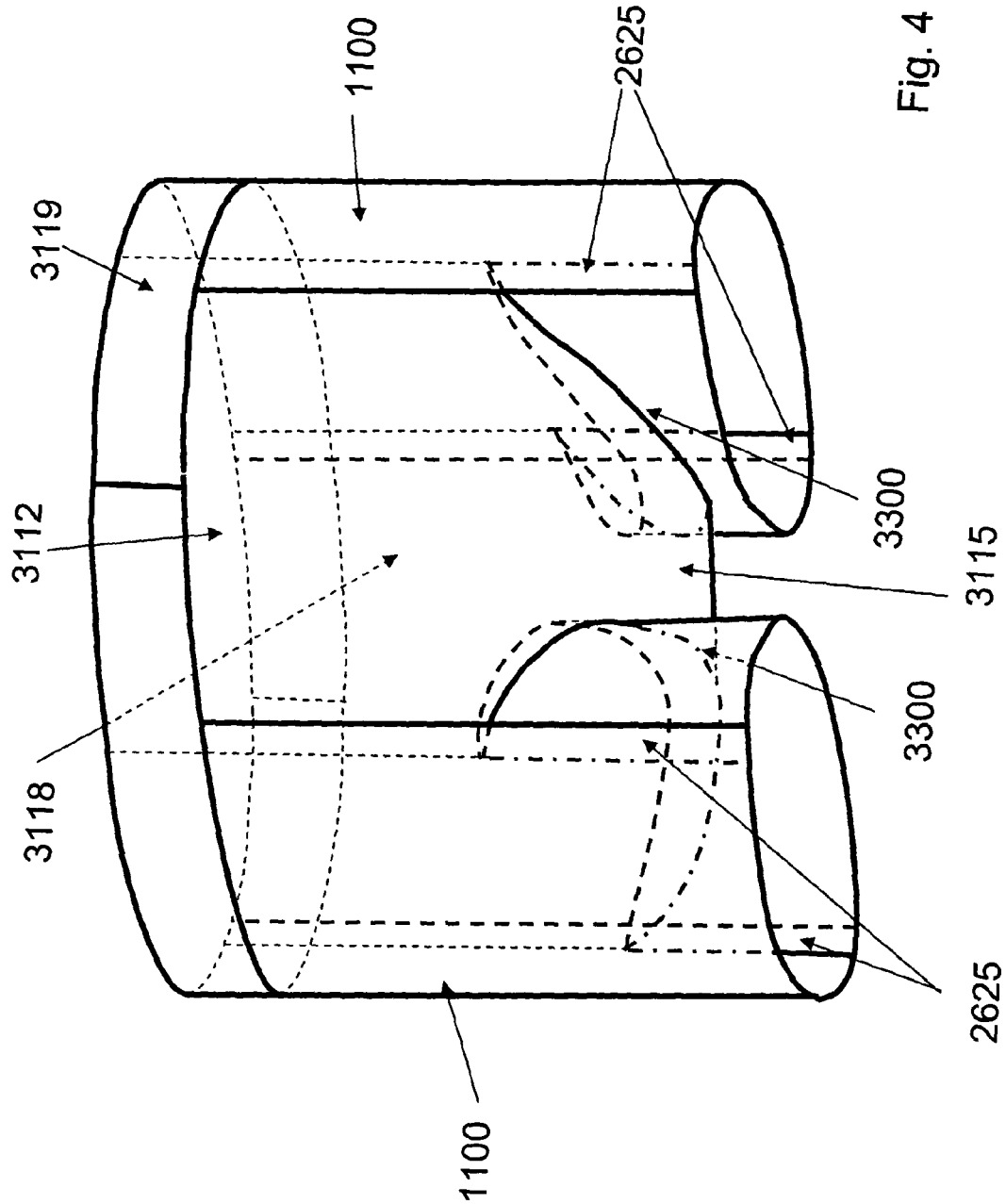

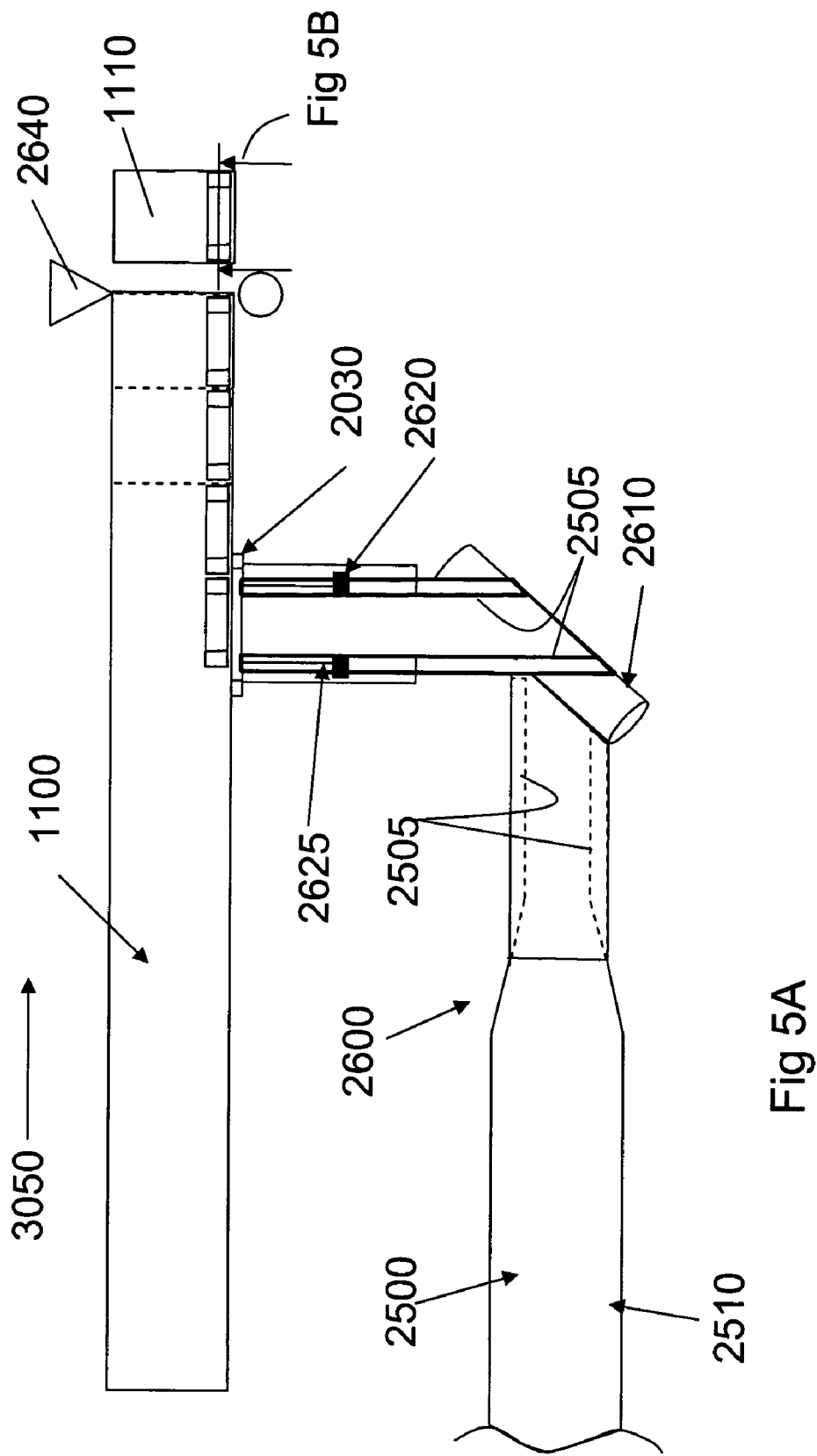

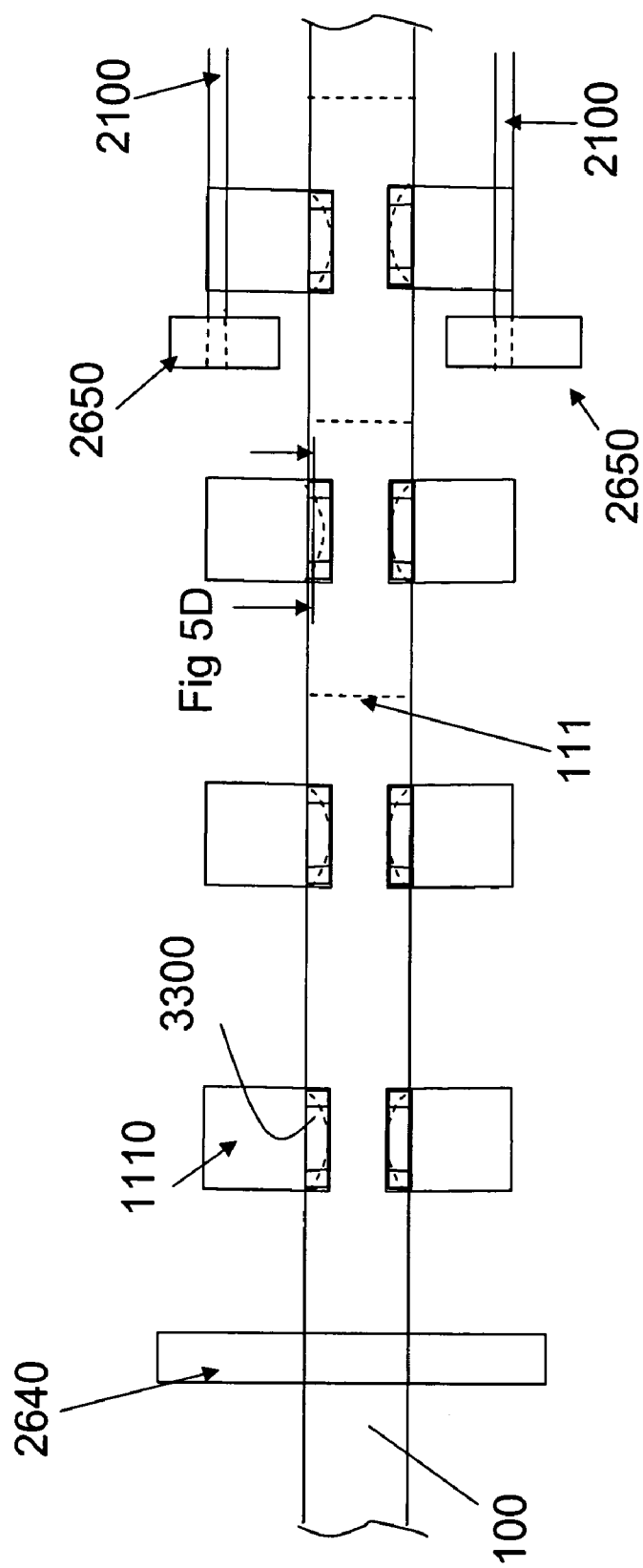

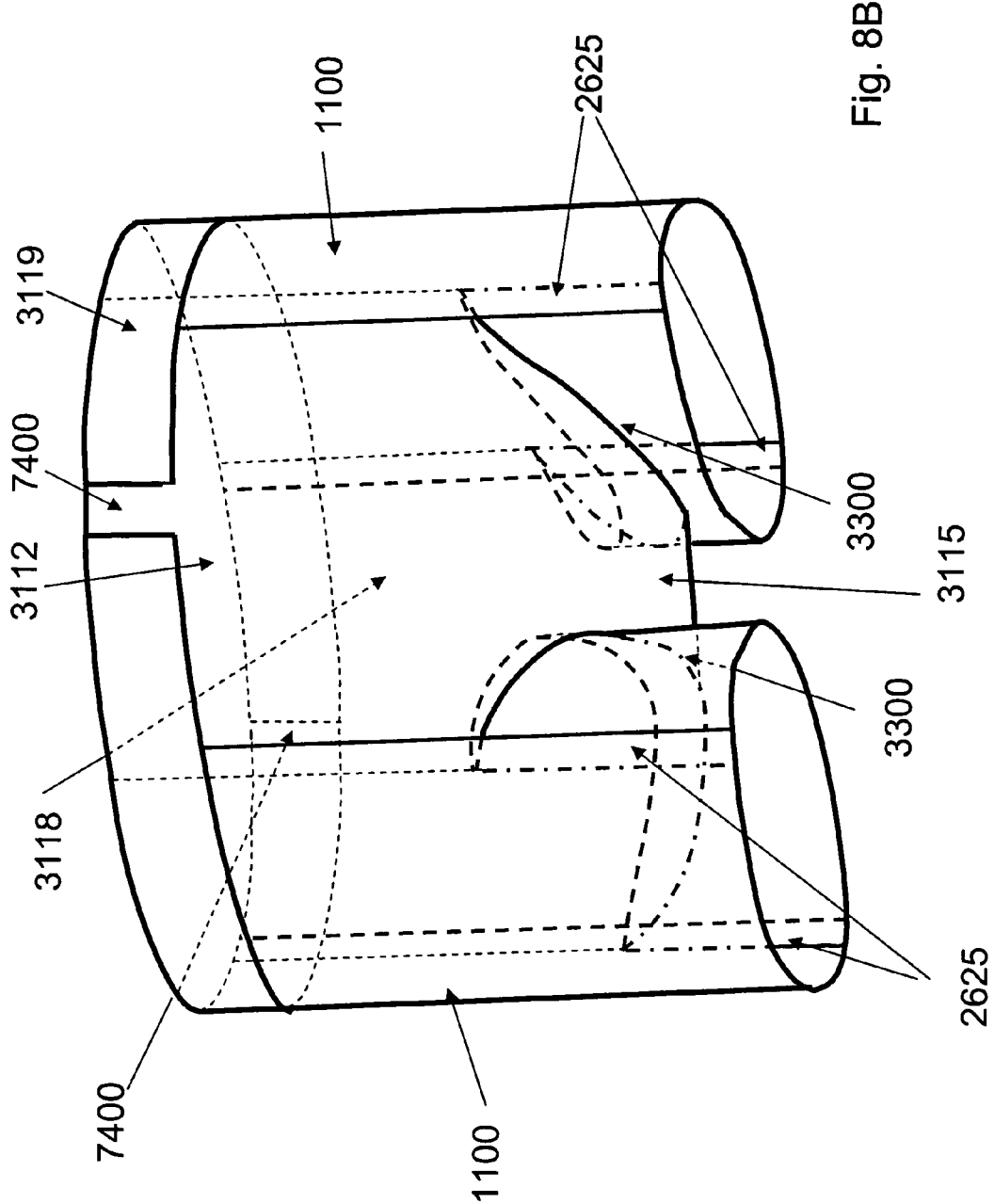

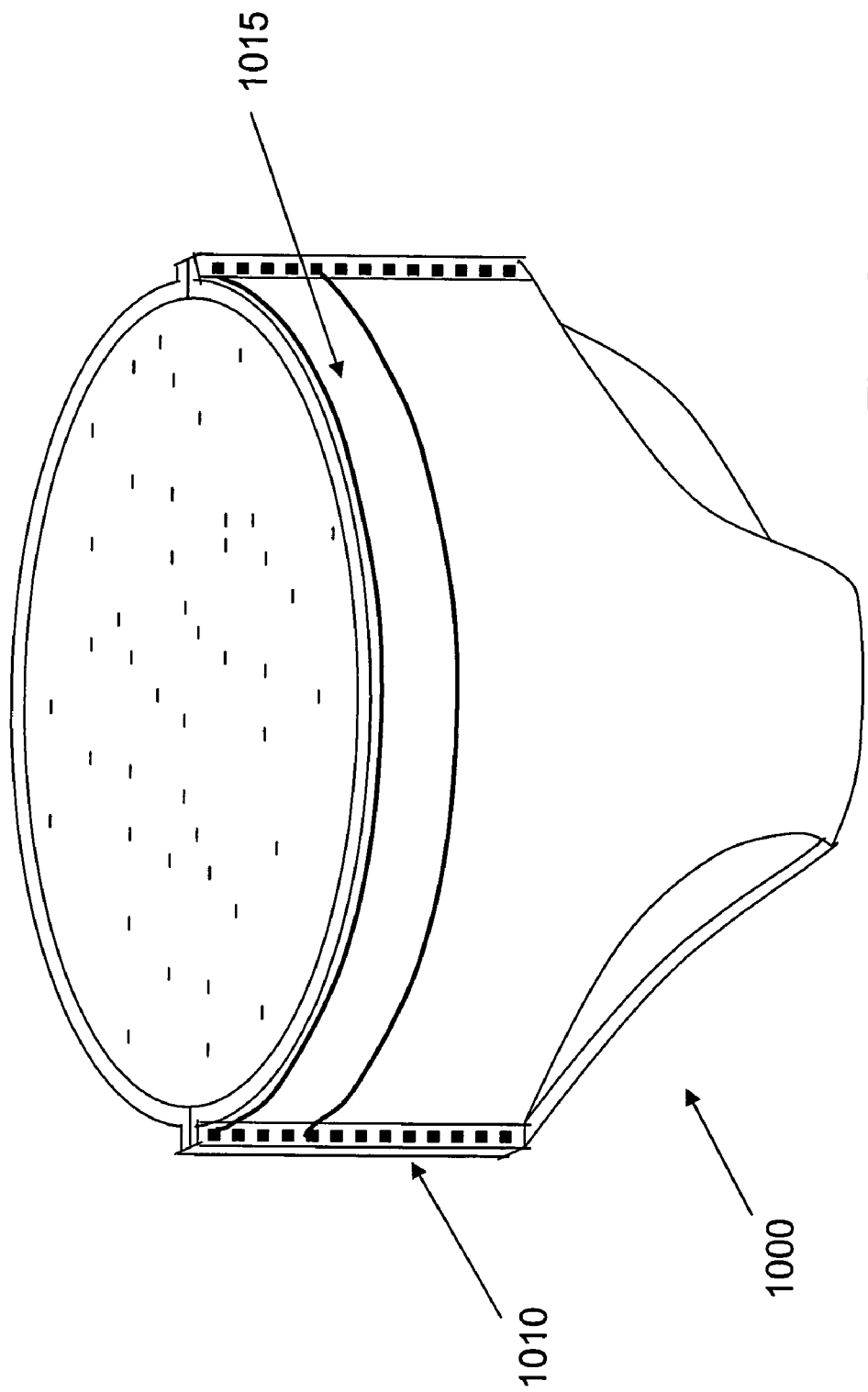
Fig. 8C – Prior Art

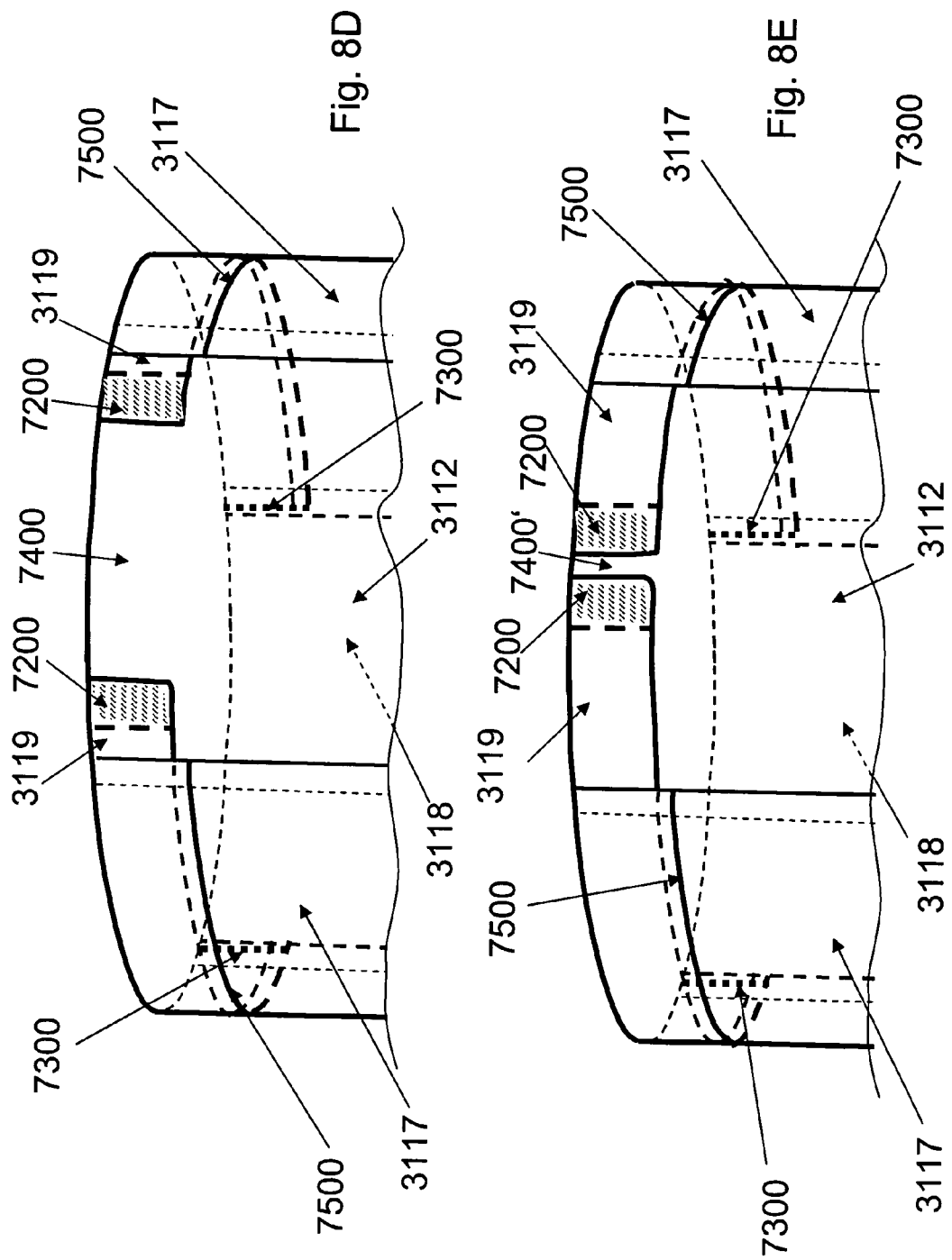

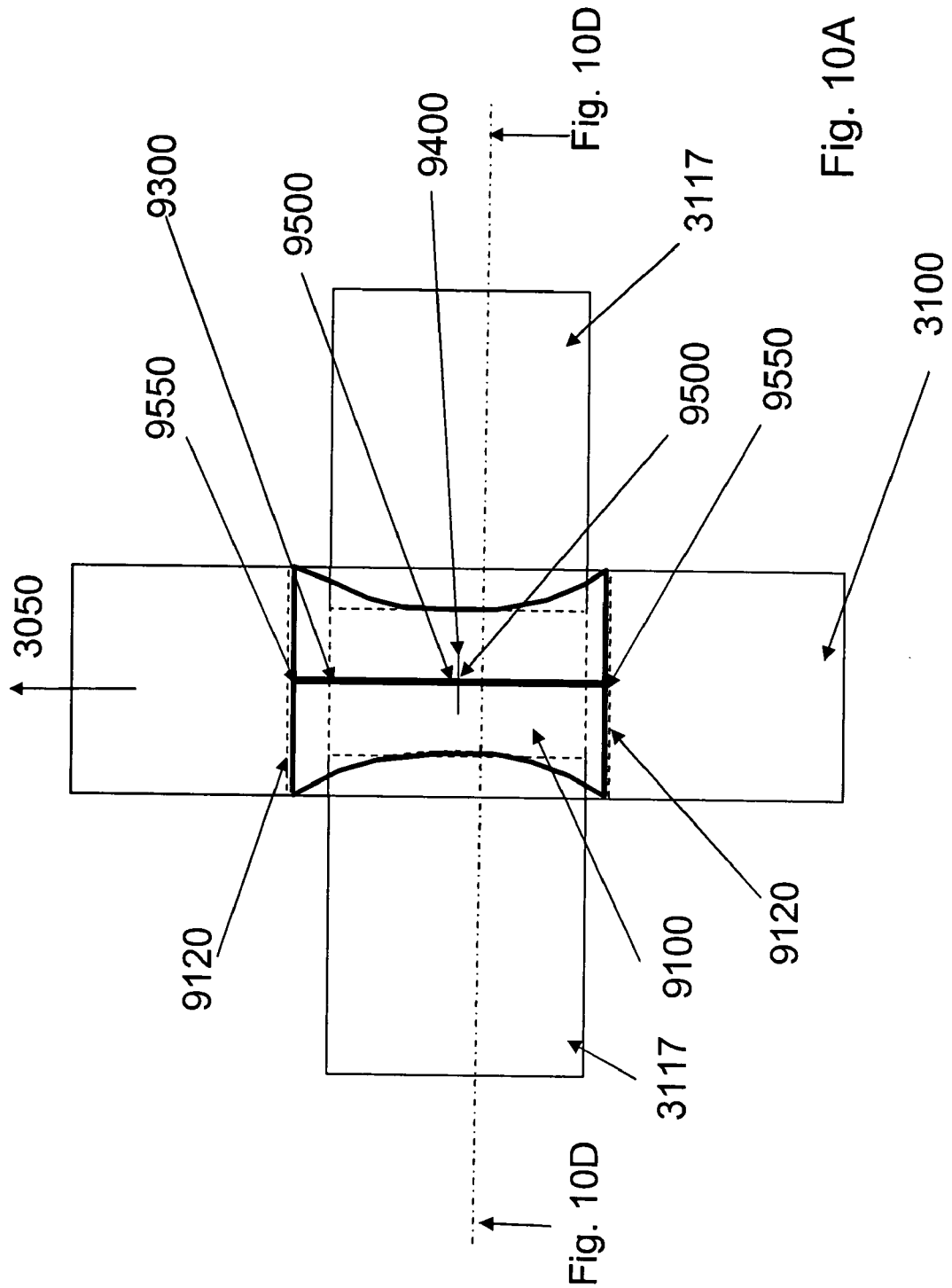

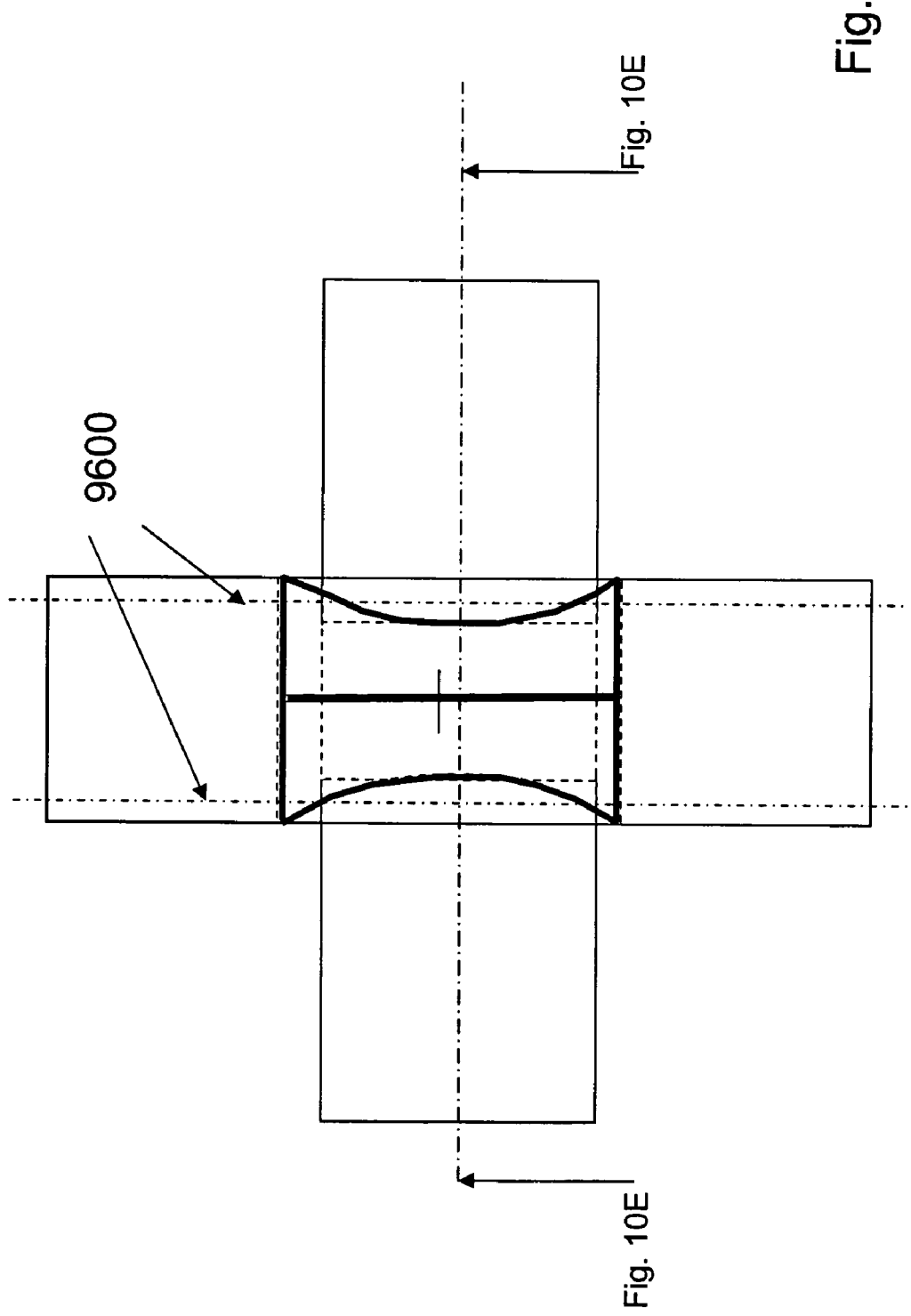

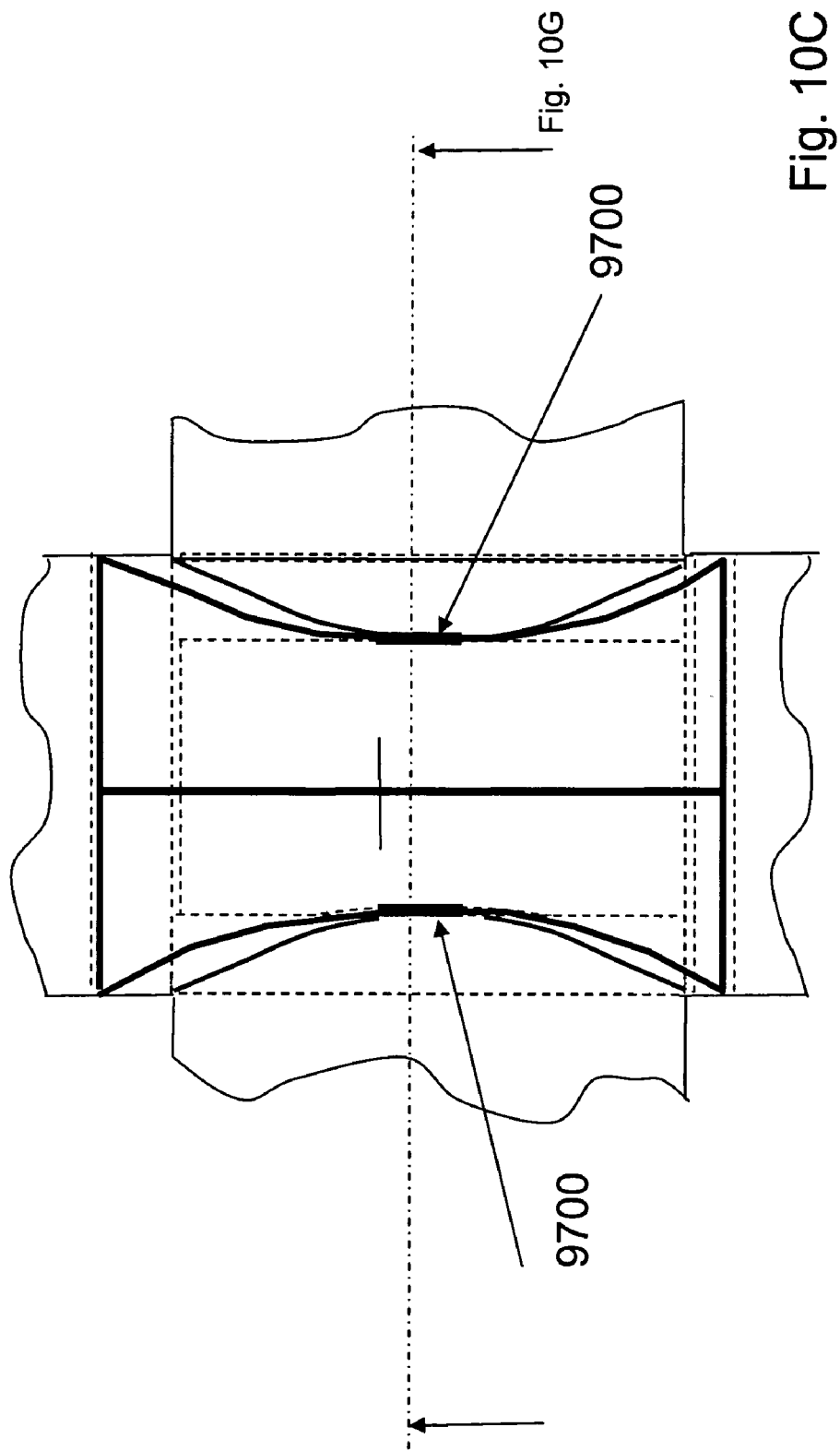

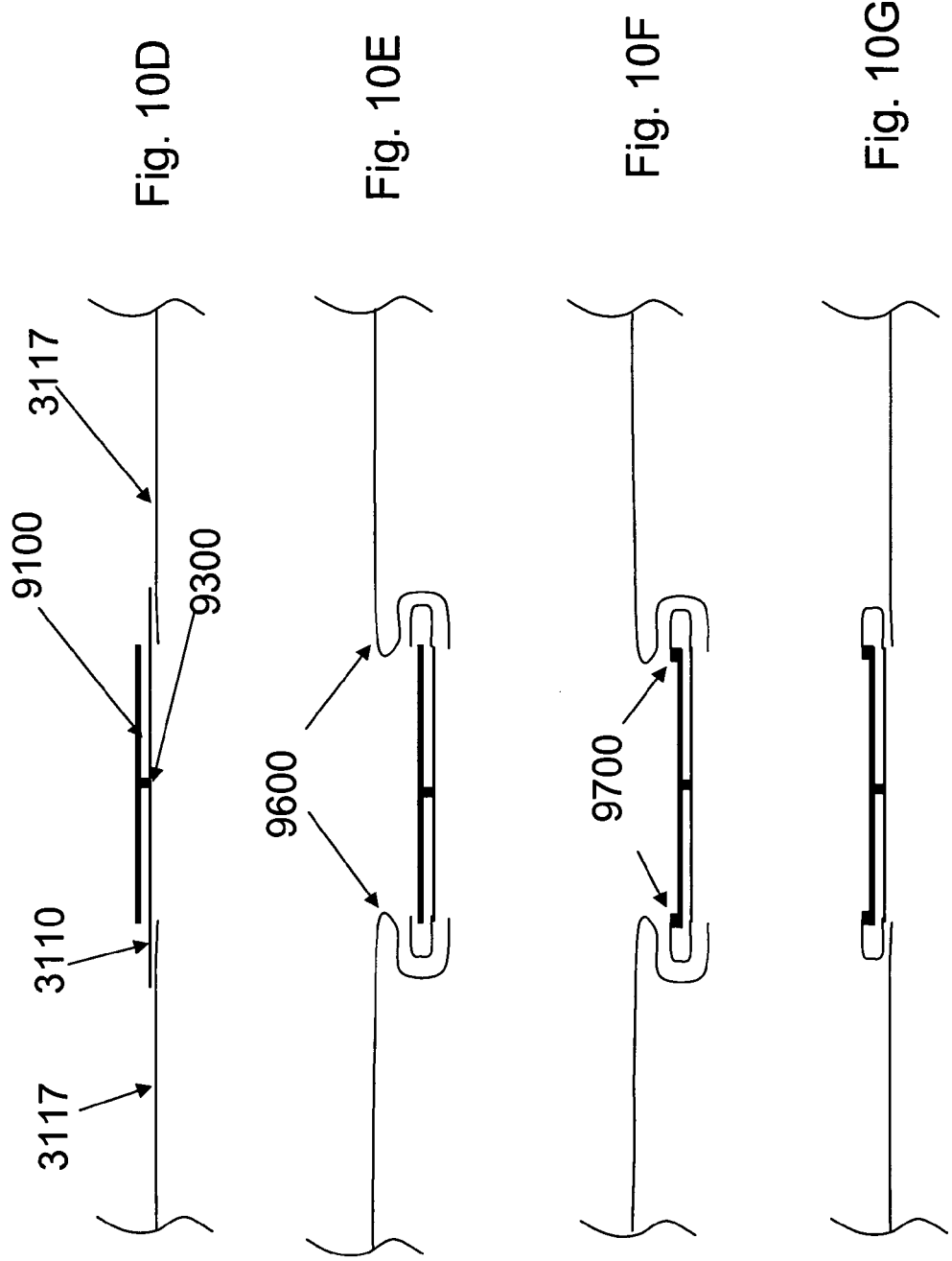

METHOD FOR MANUFACTURING A THREE DIMENSIONALLY SHAPED ARTICLE COMPRISING HIP/THIGH PANELS AND A HOOP FROM A PLUS-SHAPED BLANK, AND SUCH AN ARTICLE

CROSS-REFERENCE TO RELATED APPLICATIONS

This application is an U.S. national phase application under 35 U.S.C. §371 based upon co-pending International Application No. PCT/EP2006/00943 filed on Sep. 28, 2006. Additionally, this U.S. national phase application claims the benefit of priority of co-pending International Application No. PCT/EP2006/00943 filed on Sep. 28, 2006. The entire disclosures of the prior applications are incorporated herein by reference. The international application was published on Apr. 3, 2008 under Publication No. WO 2008/037281 A1.

FIELD OF THE INVENTION

The present invention relates to the manufacturing of an article made from web materials, such as textiles, non-wovens, films, or composites made there from. The articles have a three dimensional shape when in use and comprise a belt or a hoop structure. In particular, it can be applied to the production of wearing apparel or garments to be worn on the lower torso of the wearer, or of absorbent hygiene articles, such as disposable diapers. The present invention also relates to the equipment for making such an article, and such articles.

BACKGROUND

The industrial manufacturing of articles such as garments having a three-dimensional (3D) shape and/or comprising a closed structure, such as a belt or a hoop, conventionally employs little automation, e.g. automatic sewing of the components. The rarely used automated methods are typically limited by complex equipment designs and/or low production speeds. Such sewn articles are disclosed in EP-A-0988803, relating to a panty girdle, or US-A-2004/0098784, relating to a net pant, or WO-A-01/061093, relating to boxer shorts, however the manufacturing is not on production lines employing a continuous process.

JP01284284A2 discloses a machine for continuous sewing of an annular resilient belt-form material. The machine inserts or sews a tubular elastic belt shape body, e.g. rubber ring, to tubular cloth, e.g. trousers or a skirt, continuously. The machine sews the cloth by guiding the rubber ring by a guide device having a guide plate, bending ends of tubular cloth to make a bent part, and placing endless rubber ring in the space made by the bent part and retreats to the open end side of the bent part. In U.S. application US-A-2002/0084017, a process is described for the manufacturing of a 3D article, wherein waist elastic, an insert and a 3D skirt or trunk are combined by using an expandable/retractable fixture, which is run through a process loop such as a loop conveyor system. This process and equipment however, is complex in design, and whilst the process may run automated, there are also severe limitations in the production speed.

Considering conventional pant like articles or articles to be worn on the lower torso of the wearer, such as diapers or so called training pants, and which are manufactured on high speed production lines, these are typically based on relatively simple structures. In particular the art of making disposable absorbent articles is an area where a lot of effort has been spent against efficient manufacturing of body conforming articles, and a first generation of articles was based on essentially rectangular composites, which later were improved by narrowing the composite in the crotch region when being worn, thus in the longitudinal centre region of the article. Such articles are commonly referred to as hourglass shaped articles (refer to FIG. 3E). A variant of this design, sometimes referred to as T-shaped, is an asymmetric design, where the rear waist region of the article on the wearer is significantly wider than the front region, such that the lateral extensions of the rear regions (also referred to as "back ears") are wrapping the waist of the wearer and are connected to themselves and/or to the front region of the article.

Typically, such articles are essentially two-dimensional, i.e. made from flat panels, such as web materials, and they can be folded flat such that all connecting lines connecting various parts of the article to each other are also flat on a flat surface. Some of the designs are articles, which are pre-combined by the manufacturer, such as in a pant style, to be used e.g. as a so called training pant. Such designs comprise a waist opening and two leg openings, the leg openings separated by the crotch region of the article, and the laterally outer regions of the article corresponding to the hip region of the wearer comprise permanently or releasably connected side panels. Upon use, the side panels may be opened and re-closed e.g. for inspection of the article, or may be torn open, e.g. for removal of a loaded article.

Typically, such articles are primarily folded along a fold-line extending cross-directionally, e.g. placing front and rear ends onto each other. Additional secondary folds, such as to fold lateral extensions such as ear regions inwardly, may be folded along a longitudinal fold line.

Some of the designs as described in the above, attempt to improve the body conforming fit by introducing a three-dimensional design, whereby the article as made from essentially flat webs or panels cannot be laid flat on a flat surface with all connecting lines lying flat, too.

All such designs still have in common, that the shape is such, that, when the article is cut open along a line extending longitudinally through the side portions of the article and laid on a flat surface, the article is hourglass-shaped, i.e. narrower in the crotch region of the article than in the waist region(s).

A first approach to arrive at a fundamentally different design is described in co-pending patent applications PCT/IB05/000845, PCT/EP06/002165, or PCT/EP06/002166. Such designs comprise side portions, which are positioned—when the article is cut open or before it is assembled into its final shape—outwardly of the crotch region. Such a design may be referred to as a Plus (or +) design, as the blank for manufacturing such an article is not narrower in the crotch region but rather wider in this region, because the side-panels are arranged in this area, such that they can wrap around the outer part of the leg of the wearer. The side panel may be connected to the side crotch region of the product, i.e. to the laterally outward regions of the centre crotch region, so as to form a leg hoop, i.e. a belt like structure around the legs of the wearer during use.

Such Plus-designs exhibit great advantages in design flexibility and hence comfort of the wearer during use, without compromising sealing functionality which is desirable, e.g. in the case of absorbent articles, like diapers. As described in the mentioned documents, a particularly suitable manufacturing process employs a parallel treatment unit, such as a turret or a slide track loop, with several essentially identical treatment heads on which the articles are formed from precursor webs.

Whilst this approach allows article designs, which could hitherto not be realized on high speed manufacturing equipment, and also offers highly flexible manufacturing processes to arrive at such articles, it requires, that some of the precursor web elements need to be provided un-assembled to the treatment head, on which these will be combined and folded to form the shaped article. This involves a process unit with a high number of moving elements, respective drive and sensor means. In some cases of simpler product designs, such high process flexibility may not be required, and the related investment may not be considered appropriate.

Thus, the present invention provides a significantly simpler method to make articles with hoops such as leg or waist hoops by pre-combining essentially all web elements to an essentially flat precursor blank before this precursor blank is transferred to a treatment head, where it is folded and finished to form the article. The approach will thusly be to form a precursor blank in a "Plus-" or (+)-shape. On the treatment head, the respective "arms" of the Plus-shaped blank are folded downwards, and then adjacently lying edges are connected to form the article comprising closed structures, also referred to as hoops, around the legs of the wearer during use, and/or around the waist. In a preferred embodiment, the article elements are arranged during the manufacturing such that the front to back orientation in the article corresponds to the machine direction, while laterally outwardly extending side panels are oriented in cross machine direction.

Optionally, elements for forming a closed hoop in the finished article, such as waist bands, oriented and optionally elasticated along their MD direction can be attached to the side portions. As a consequence, if the article comprises a waist band, this may be connected in the front and back regions of the article, rather than in the side regions as will be inevitably the case for the conventionally manufactured articles.

The centre piece web may be cut into individual pieces on or prior to being transferred to the parallel treatment unit, e.g. after the side portions are attached thereto. In an alternative process set-up, the sequence of process steps may be such that the centre piece web is cut in discrete pieces before the laterally outwardly extending side portions are attached to the discrete centre pieces. Such sequence is particularly useful if the distance between subsequent centre pieces is to be altered, and if there are continuous webs connecting e.g. the side portions of subsequent cut pieces e.g. at their outer perimeter.

Preferably, although not necessarily, at least one major element of the article should be essentially unitary when the article web is transferred to the parallel treatment unit, to ease transfer to this unit. In the case of articles without a waist band, the centre piece of the article may be essentially unitary, i.e. to extend essentially along the full length of the article (from front through crotch to the rear), optionally combined with other elements, such as leg hoop and side-panel materials, prior to the positioning on the forming head of the parallel treatment unit, where the article web is cut, and the thusly obtained discrete articles are formed and finished. In articles with a waistband, the centre piece web may be cut in discrete pieces, and those pieces may be connected to each other by unitary waist band webs.

Thus, in one aspect, the present invention is a method for manufacturing shaped articles, which comprise at least one closed hoop structure and at least a primary and a secondary web material. The manufacturing can be performed on a high speed manufacturing equipment, which comprises a web supply means, a blank forming means, a means for cutting the blank from the web into discrete elements, a means for transferring the blanks to a parallel treatment unit, preferably a turret or an endless track. This parallel treatment unit comprises at least two web treatment sections for parallel treatment of the blanks, whereby each parallel treatment section further comprises a treatment head. Such a treatment head comprises a centre plate, being positioned essentially parallel to the surface of the parallel treatment unit, to which the blanks are transferred, longitudinal extension plates which are positioned or extending forwardly and rearwardly of the centre plate along the overall manufacturing direction of the parallel treatment unit, and which are pivotable such that the forward or rearward ends can be turned downwardly away from the surface of the parallel treatment unit whilst the respective other ends of the extension plates remain adjacent to the centre plate. Optionally, the treatment head further comprises laterally extending side plates, which may also be pivotably connected to the centre plate. The pivoting of the longitudinal and/or lateral extension plates may be achieved by drive means selected from the group of mechanical drives, preferably cam drives, pneumatic drives, or electric drives, preferably servo drives. The centre plate and/or the longitudinal and/or lateral extension plates preferably comprise a web fixation means, preferably a vacuum suction means. The treatment head further comprises connecting means for connecting portions of the blank to other portions of the blank, and fixation means to temporarily hold web materials and/or the blanks. The method thus comprises the steps of:

(a) preparing a pre-cursor blank, which comprises a centre piece comprising a primary web. The centre piece consists of a centre region, and a front and a rear region extending longitudinally from the centre region. The pre-cursor blank further comprises side portions extending laterally outwardly of both sides of the centre region comprising the secondary web, thusly forming a Plus-shaped precursor blank;

(b) transferring the pre-cursor blank to the parallel treatment unit comprising the treatment sections, each treatment section comprising a treatment head;

(c) temporarily attaching the centre region of the precursor blank to the surface of the centre plate of the treatment head which is out- or upwardly facing, and the front and rear regions to the longitudinal extension plates of the treatment head, whilst these are in an upwardly folded position essentially aligned with the centre plate;

(d) separating the primary web into individual pieces, before or after having formed the precursor blank;

(e) pivoting the outward front and rear ends of said longitudinal extension plates downwardly away from the surface of the parallel treatment unit whilst the front and rear regions of the precursor blank remain attached thereto;

(f) folding the side portions of the pre-cursor blank downwardly, so as to bring the side margins of the front and rear regions and the side margins of the side portions into an adjacent or overlapping positioning;

(g) connecting respective side margins, thereby forming a closed article comprising a hoop;

(h) optionally further treating the article;

(i) removing the article from the parallel treatment unit.

Optionally, the method can comprise a further step of (j) adding a further web material to the pre-cursor blank.

This further web material may be essentially endless and may connect the side portions of consecutive pre-cursor blanks, preferably the laterally outward perimeter of the side portions. Preferably, this further web material is separated into segments after the precursor blank has been transferred to the treatment head, and after the longitudinal extension plates with the front and rear region attached thereto have been downwardly folded, and more preferably, this separation is executed essentially concurrently to connecting the cut edges together to form a closed hoop.

During step (a), the pre-cursor blank may comprise cut lines, which extend from the lateral outward perimeter inwardly. The side portions and the centre piece are connected by means of a connecting line or region essentially parallel and corresponding in cross-directional extension to the cut line. Also during step (a) of this method, a further material can be added for forming a leg hoop with the side portion material.

In a preferred embodiment of this method, the step (e) is executed prior to step (f) so as to create an overlap connection of the front and rear regions with the side portions forming the leg/thigh panel, such that in this overlay connection the front and rear regions are positioned outwardly, relative to the wearer during use, of the leg/thigh panels.

In a further aspect, the present invention is an article for being worn on the lower torso of a wearer comprising leg hoops for encircling a part of the upper thigh regions and a waist hoop for encircling the waist of a wearer during use. The article may further comprise a centre piece comprising a web material comprising a front region for being positioned in the front abdominal region of the wearer, and a rear region for being positioned in the lower back region of the wearer, and a centre region for being positioned in the crotch region of the wearer, and two hip/thigh panels comprising web materials for being positioned on the hips of the wearer and extending downwardly into at least the upper thigh region of the wearer. In a particular embodiment, the article may further comprise a further web material for being positioned on the inner thigh region of the wearer. In this aspect of the invention, the hip/thigh panels are connected to the centre region of the centre piece essentially only adjacently to the front respectively rear region, thereby forming the leg hoops during use. Further, the hip/thigh panels are connected to the front and back regions of the centre piece, thereby forming the waist hoop. The centre region forms a 3D/cup shape sustained by curve-linear fold lines in the lateral outward position of the centre region and by the fold lines forming connecting lines, or a perimeter of a connecting region between the centre regions and the optional further material for forming the leg hoop, if present.

The article may further comprise further material comprised in said waist hoop, which is essentially unitary within the hip regions, and which is either closed by being connected in a region corresponding to the front and/or back region of the centre piece or which forms a gap positioned in the front and/or rear region of the article. In a preferred execution, the article comprises a drawstring-type waist element, which allows easy adjustment of the gap width, e.g. by a caregiver.

Optionally, at least the centre piece further comprises liquid absorbent material and a topsheet positioned between the absorbent material and the user during use.

A particular embodiment is an article comprising an additional secondary topsheet positioned between the topsheet and the wearer during use. Preferably, the secondary topsheet is positioned at least in the centre region of the centre piece, overlaying at least partially the topsheet, and it may be connected to the topsheet in the region of the centre piece, as well as to the leg cuff forming materials in a region laterally outwardly/upwardly positioned relative to the folding or connecting line, or the perimeter of connecting region. This secondary topsheet comprises an opening for being positioned in the region of the anal opening of a wearer during use, which has an MD and an CD extension and a respective perimeter at least during use. The article may further comprise at least two elastic elements, each connected to at least a point of the perimeter or in proximity of the perimeter of the opening, whereby each two connection points are in a opposing position relative to the centre of the opening, and at least to a connection point of the topsheet or the secondary topsheet, the point being positioned outwardly away relative to the centre point of the opening, thereby creating a force to sustain the opening. In a specific embodiment, the secondary topsheet comprises a cross-directional cut line so as to form the opening positioned in the region of the anal opening of the wearer during use, wherein the elastic elements, preferably elastic threads or bands are positioned essentially aligned with the longitudinal centre line of the article. Further, the elastic elements are connected to a point on the perimeter of the cut line or to a point in the proximity of the cut line and to a point longitudinally away from the cut line, preferably in the waist region of the article, such that the tensioning of the elastic elements sustains the opening formed by the cut line.

The portions as being connected to the primary web to form the blank may be essentially of rectangular or trapezoidal form, but may also comprise a curvelinearly shaped perimeter. The side portion material may also be apertured by having openings, or may have slits, preferably in MD orientation, and preferably in a predetermined pattern.

The connecting means for the various connections in this article may preferably be glue bonding, thermo bonding, mechanical fastening means, or adhesive tape fastener.

The article may further comprise a tear line for allowing easy tearing at a predetermined location, such as to allow inspection while it is worn, and it may further optionally comprise a re-closeable connecting means arranged to re-connect the parts as separated by the tear line.

The article of the present invention is particularly suitably used as a disposable absorbent article, a baby or adult incontinence article, a training pant, a feminine care article, a menstrual pant, or pant shaped underwear.

BRIEF DESCRIPTION OF THE FIGURES

FIG. 3 B—shows a magnified view of the connecting regions;
FIG. 3 C—shows a perspective view of closed product;
FIG. 3 D—shows a magnified view of the connecting regions for a different embodiment;
FIG. 3 E—hourglass shaped product (prior art);
FIG. 4—Article with overlap leg cuffs/side panels;
FIGS. 5 B and D show a cross-sectional view through certain sections of the blank;
FIG. 8 C shows a perspective view of a conventional Article.

FIG. 10 A to G—show schematic views of the blank during certain process steps of the manufacture of an article comprising a secondary topsheet.

Equal numerals in various Figures refer to corresponding elements.

DETAILED DESCRIPTION

Figure 1A:
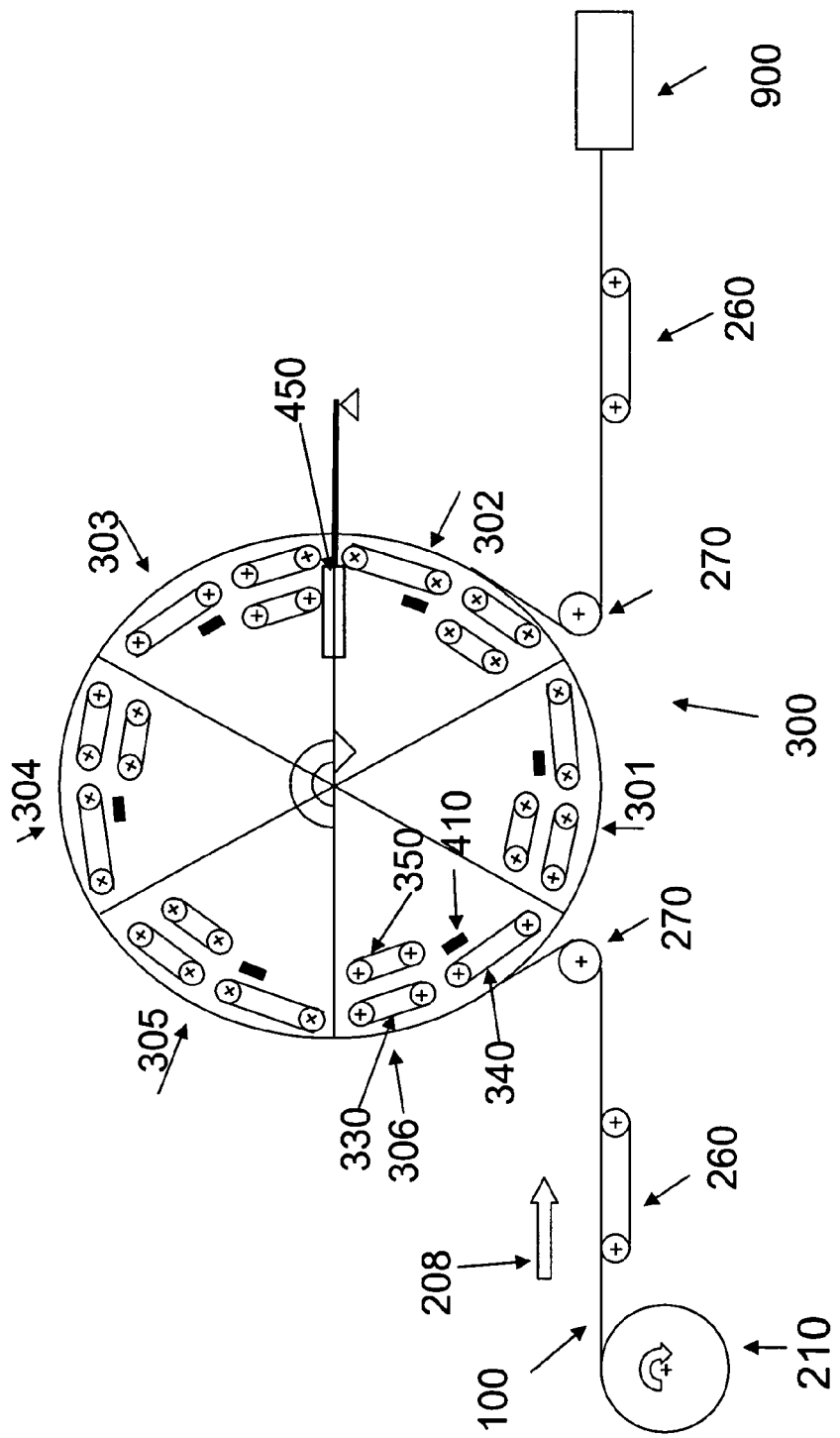
FIGS. 1 A, B depicts schematically process set ups of the prior art.

In the following, the present invention is explained in more detail by referring to diapers and pant like structures, to be worn in the lower region of the torso of a wearer. However, this should not be understood in any way limiting for the invention. A skilled person will readily be able to transfer the teachings to the manufacturing of other garments, such as T-shirts and the like.

Thus, in one aspect, the present invention is an industrial manufacturing process for garments, such as pant like structures or disposable absorbent articles produced from web materials in an essentially continuous process. The present invention allows to replace existing processes and the corresponding equipment completely, but it is also suited to be integrated into existing processes to perform only certain process steps in the overall manufacturing process. The present invention presents in certain aspects an alternative to the process as described in PCT/EP06/002165, which is incorporated herein by reference for the general teaching of suitable materials and the general process lay out, as well as for details of the execution of particular elements, such as web support means, and/or web handling means, such as vacuum boxes and the like. Thus, FIG. 1 A shows process flow chart and a schematic equipment set up as disclosed therein.

In this process, a web material 100 is fed from a web supply means 210 via web support and guide means (260, 270) and a parallel treatment unit, here shown as a rotating turret 300, at an overall process speed and direction 208 to the process end section 900, from where it may be distributed to further processing step, or where it may be packed. The turret comprises several parallel treatment sections 301 . . . 306, wherein the web 100 is treated, such as folded, or combined with other webs. This treatment is achieved by positioning the web on web support means 330, 340, and 350, which may be operated at independently programmable speeds and thus may, for example, form a specific cross-directional fold in the web. Further, a web treatment head 410, positioned in each of the parallel treatment sections 301 . . . 306 may cooperate with a treatment tool 450, here shown stationary such that one such tool can cooperate with all of the treatment heads as they pass by the tool upon rotating, such as combining specific sections of the web to other sections.

The originally essentially continuous web 100 may be cut into discrete pieces prior to be fed to the turret, on the turret, or after being removed from the turret.

An important element of this equipment is the use of web support means 330, 340, 350 arranged in the web treatment sections 301, . . . 306, such as programmable vacuum belts to transfer the web 100 to a treatment head 410, after a cross-directional fold has been formed by appropriate adjustment of the transport speed and/or direction of the web support means. Adjacently positioned sections of the webs are respectively connected on this treatment head, thereby forming the basic form and shape of the article.

Figure 1B:
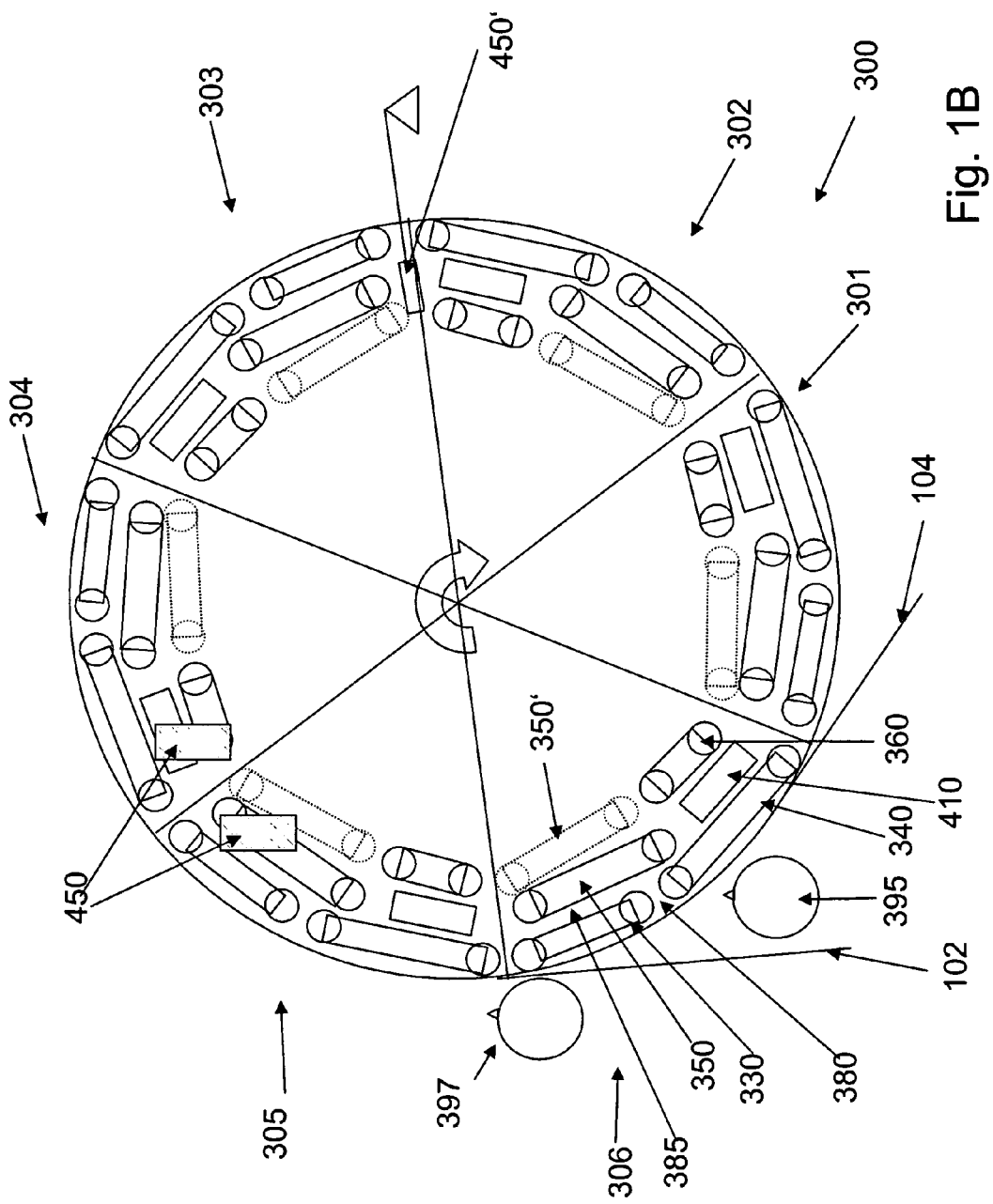

In a configuration as schematically depicted in FIG. 1 B, two webs 102 and 104 are fed to the treatment sections 301 . . . 306 of a parallel treatment unit, here a turret 300, and separated to the appropriate length, e.g. by cutting means 395, 397. Upon appropriate movement of the web support means 330, 340, 350, and 360, and further by radial movement of at least one thereof—here shown by the position 350'—the first web 104 is CD-folded and moved through the gaps 380 and 385 to be positioned on the treatment head 410, where it is combined with the second web material 102 upon further rotation of the turret, e.g. by combination tools 450 or 450'.

This setup provides a high level of flexibility, both for making product variants, and for making different sizes of a specific product. However, this level of flexibility may not be necessary or desirable, like when the product to be made is clearly defined or of a single size.

Figure 2:
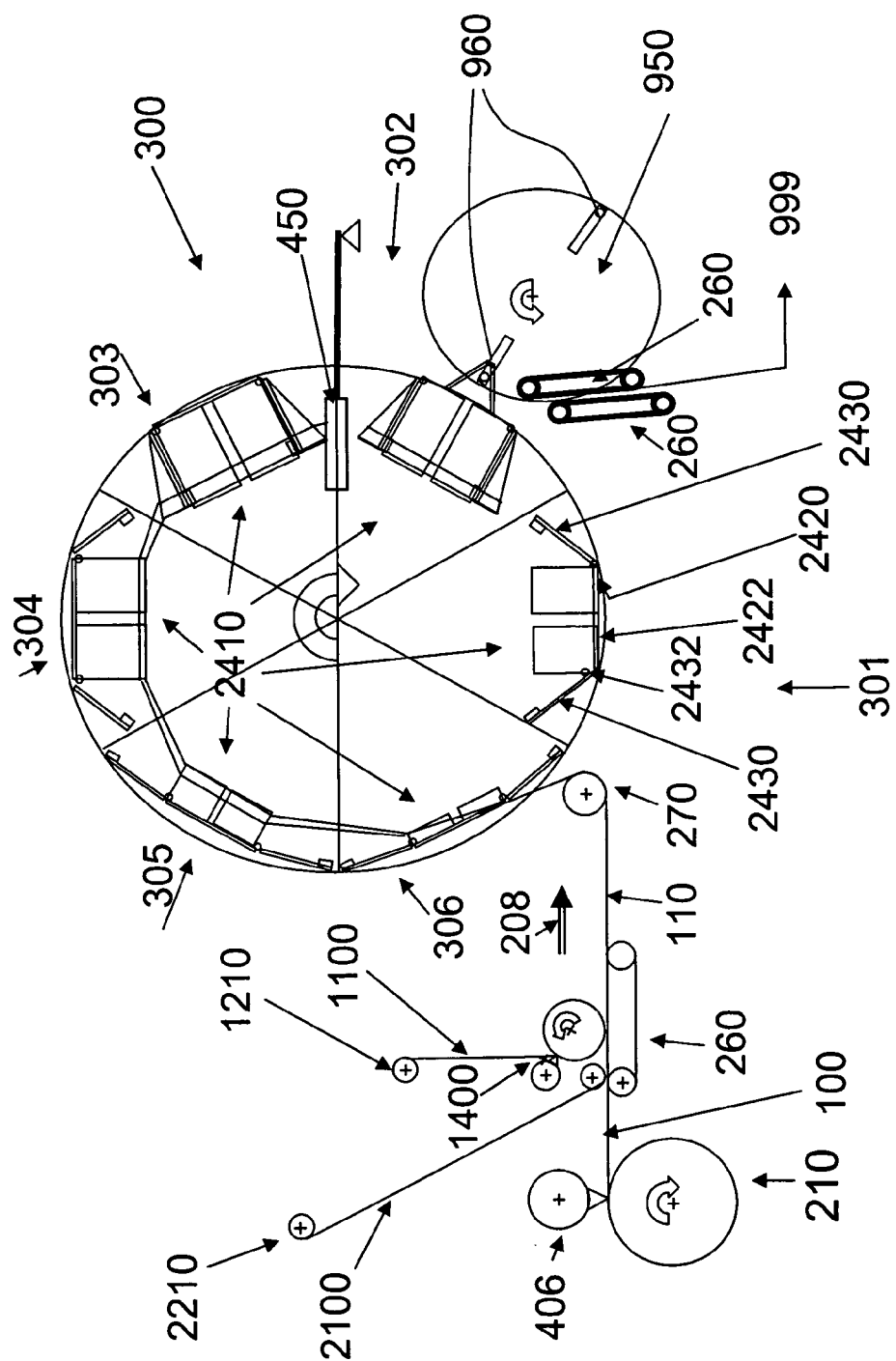
FIGS. 2 A and B depict schematically processes according to the present invention.

Thus, the present invention provides a simpler, yet high speed compatible alternative for a process and an equipment design, for which one embodiment is schematically depicted in FIG. 2A.

In analogy to the prior art process described hereinabove, a primary essentially endless web material 100 is provided on a web supply means 210 via web support and/or guide means 260, 270 at an overall process speed 208, which may be as high or higher than 8 m/sec web speed, which may correspond to over 1000 articles per minute. For certain embodiments the primary web material may be cut by a separation means 406 prior to being combined with other materials to form the pre-cursor.

A second essentially endless web material 1100 as being supplied from a second web supply means 1210 is cut e.g. by a cut and slip unit 1400 in discrete pieces, transferred to the primary web and attached such that it extends on both sides laterally outwardly of the primary material, to regions which will correspond to the crotch region when the finished article will be worn. This material may be supplied essentially unitary, and separated on line, or two web supply means may provide separate webs. Optionally, these material(s) may already form a composite material, such as being partly elasticated, such that e.g. the non-elastic portion is connected to the centre piece, whilst the elastic portion may be positioned laterally outwardly thereof, e.g. to later form a part of waist hoop.

Optionally, a further essentially endless web material 2100 may be supplied from a further web supply means 2210, such as to form a waist hoop in a finished product. This further web material may be in the form of two relatively narrow material stripes, optionally elasticated, which extend essentially parallel to the orientation of the centre piece material 100, and which may be connected to the laterally outward edges of the second web material 1100.

The primary web 100, the secondary web(s) 1100, and optionally the further web(s) 2100 can be combined by conventional means, such as so called cut- and slip units, 1400, and conventional connecting means to form a pre-cursor web or a sequence of pre-cursor web pieces 110, as depicted in FIG. 3A as a piece of pre-cursor blank 3000 and discussed in more detail herein below.

The pre-cursor blank 110 is then transferred to a parallel treatment unit for parallel treatment of at least two blank pieces 110, here shown as rotatable drum or turret 300, comprising at least two web treatment sections, here shown as six units 301 to 306. Each of these sections comprises a treatment head 2410, which further comprises (i) a centre plate 2420 having a first surface 2422 oriented outwardly of the rotating drum 300;

(ii) two longitudinal (in the direction of movement of the web; x-direction) extension plates 2430, which are pivotable such that the forward or rearward ends can be turned downwardly or inwardly away from the surface of the parallel treatment unit whilst the respective other ends of the extension plates remain adjacent to the centre plate. This can be by connecting these plates by a hinge 2432 to the centre plate 2420, so as to allow pivoting them downwardly to an essentially perpendicular position to the centre plate. Alternatively, these extension plates may be moveably affixed to the frame of the treatment section.

(iii) and optionally two side plates (not shown in FIG. 2), being positioned laterally outwardly to the lateral side edges of the centre plate 2420 in an essentially rectangular downward (towards the centre of the drum) position.

Whilst the plates and surfaces of the treatment head are generally described as being flat, this refers to the overall extension of these plates or surfaces, whilst the exact shape may be somewhat rounded or edged. Thus, the centre plate may have a shape corresponding to the surface of the turret (i.e. the segment of a cylinder) or approximate the shape of the finished article, e.g. be adapted to the surface of the lower torso to be wrapped by the finished product, or each longitudinal extension may be formed of two plates in an angular configuration.

The webs may be treated, such as by connecting specific sections to other sections, such as by connecting tools, so as to form the finished article 999, and may be removed from the turret 300 such as by using a removal means, here shown as rotating disk 950 positioned adjacent the turret 300 and comprising one or more moveable finger(s) 960 arranged to engage into the treatment head 2410 and the article positioned thereon, so as to allow pulling out of the formed article 999 upon further rotation of the turret and the at least one rotating disk, optionally by using further web support or guide means 260.

With such a set up of the equipment, the preferred process sequence of forming an article according to the present invention as depicted in FIGS. 3A to D comprises the following steps, which are further discussed in more detail herein below:

(a) preparing a pre-cursor blank 110 which comprises a centre piece 3100 comprising the primary web 100, consisting of a centre region 3115 and a front (3112) and a rear (3118) region extending longitudinally from the centre region, further comprising side portions 3117 extending laterally outwardly of the centre region comprising a secondary web 1100, thusly forming a Plus-shaped precursor blank, (b) transferring the pre-cursor blank 110 to a parallel treatment unit 300 comprising treatment section 301 . . . 306, each treatment section comprising a treatment head 2410;

(c) temporarily attaching the centre region 3115 of the pre-cursor blank 110 to the surface 2422 of the centre plate 2420 of the treatment head 2410 which is out- or upwardly facing, and the front (3112) and rear regions (3118) to the longitudinal extension plates 2430 of the treatment head 2410, whilst these are in an upwardly folded position essentially aligned with the centre plate;

(d) separating the primary web into individual pieces, before or after having formed the precursor blank;

(e) pivoting the longitudinal extension plates 2430 downwardly whilst the front and rear regions remain attached thereto;

(f) folding the side portions 3117 of the pre-cursor blank 110 downwardly, so as to bring the side margins of the front and rear regions (3113 and 3123, respectively) and the front/rear margins 3116 and 3126 of the side portions 3117 into an adjacent or overlapping positioning;

(g) connecting respective side margins, thereby forming a closed article comprising a hoop;

(h) optionally further treating the article;

(i) removing the article 999 from the parallel treatment unit.

Detailed Discussion of the Individual Process Steps:

Ad (a) (Preparing a Pre-Cursor Blank):

The pre-cursor blank 110 is formed from a web material 100, which may be an essentially continuous web or an essentially continuous sequence of web pieces as cut from a continuous web. Typically, but not necessarily, the web material 100 will be supplied oriented such that the front to back direction of an article made of a web piece cut from the web corresponds to the MD direction of the web material 100 as well as to production direction of the equipment (MD), generally depicted as MD-direction 3050.

Figure 3D:
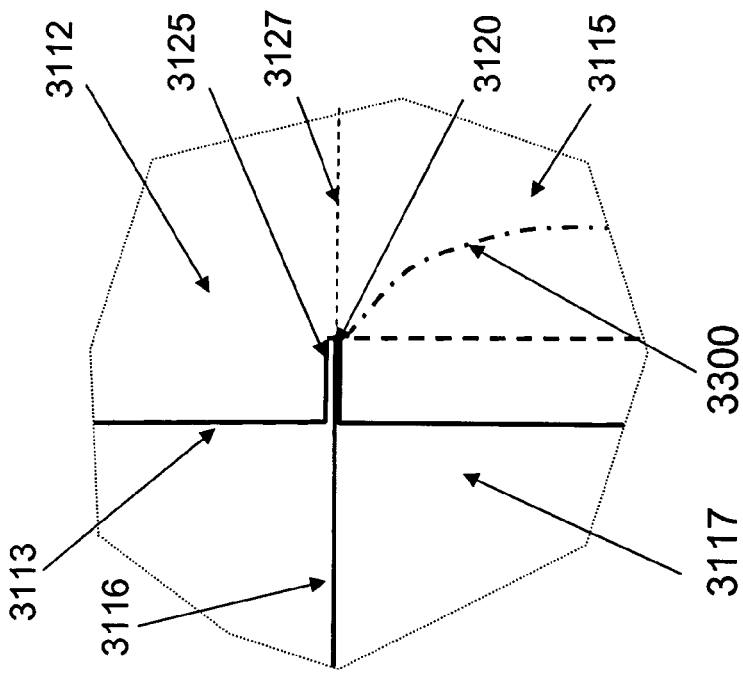
FIG. 3 A—represents a Plus-shaped pre-cursor blank laid out flat.
Figure 3B:
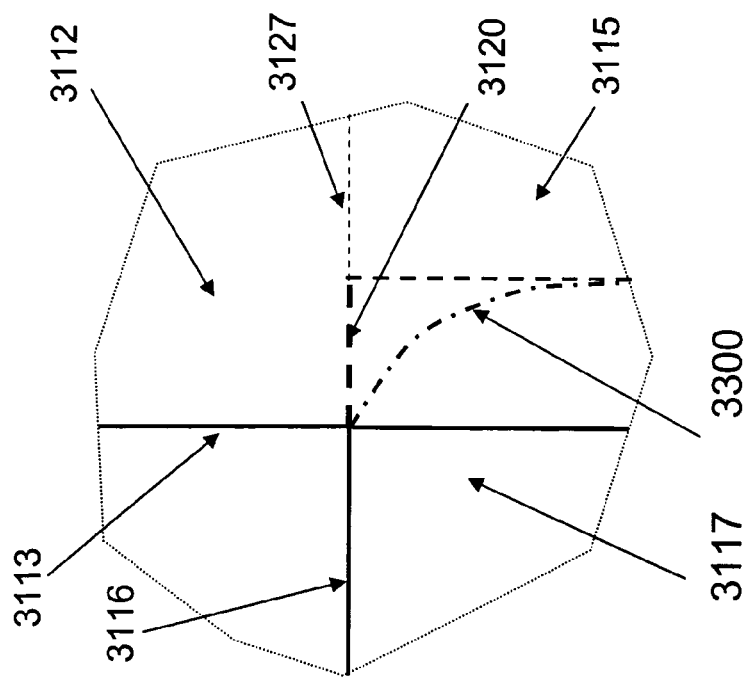

A suitable pre-cursor blank is depicted in FIG. 3A, showing the principle of a Plus-shaped precursor blank 3000, and 3C, showing a perspective view of an article 999 made from such a blank with a centre piece 3100, comprising a front region 3112, a rear region 3118, and a connecting centre region 3115, arranged along the machine direction 3050 of the web 100, which preferably corresponds to the machine direction of the parallel treatment unit 300. Two side portions 3117, which form the hip/thigh panels of the finished article, are extending laterally outwardly of the centre region 3115 of the centre piece 3100. FIG. 3B shows a magnified view of one of the four connections, for the embodiment of a blank with extra material applied as to cover the inner thigh regions of the leg hoop, additionally depicting a connecting region 3120, whereby the side portions 3117 are connected to the centre region along the demarcation line 3127 between the centre and the front/rear region. The connection may be achieved by conventional means, such as by gluing, heat bonding and the like. The connection is preferably executed in the form of a fine line, but may cover a certain area, which, however, should be minimized for fit reasons. For the embodiment of a product without an extra material applied as to cover the inner thigh regions, slits or cuts 3125 adjacently to the connecting region are performed along the demarcation lines 3127 between the centre and the front/rear region, preferably while the connecting lines or regions 3120 are made, FIG. 3D. Whilst this cut line is shown as a straight line with a cross-directional orientation, it may be arranged in other angles, but not parallel to the side margin of the centre region in that section. The cut line may also be executed curve-linearly, which, however, might make the creation of the connecting line/region, which should essentially follow the cut line, more difficult. The length of the connecting lines or regions and the cut line impact on the form and shape of the leg cuff and thus of the leg opening, which is later formed on the forming head. As the side portions 3117 are not connected to the centre region 3115 other than by the connecting line or region, they will loosely overlay the centre piece in the overlay region 3131, from which later the leg cuff and leg opening 3130 will be formed in the finished article.

The Plus-shaped blank, as depicted in FIG. 3A to D, may further comprise a further material 3119 arranged to form a waist hoop in the finished article. To this end, an essentially endless narrow stripe of this material, which is preferably elasticated, is attached to the outward edges of the side portions 3117.

Additional elements may be added to the pre-cursor blank, such as in case of manufacturing absorbent articles, the absorbent members (cores) may be combined with any of the web materials or with the pre-cursor blank. In contrast to conventional articles, especially the herein above referred to hourglass shaped articles, the cup-like shaped centre region of the article according to the present invention allows—in addition to improving sealing performance against leakage especially in the thigh region—to position further liquid absorbing capacity in the crotch region, or even in the leg cuffs, as formed by the side portions and laterally outwardly positioned regions of the centre region.

Whilst the FIG. 3 shows an isolated Plus-shaped blank, consecutive blanks may be connected to each other on the production line, such that the centre pieces may be connected before these will be cut, and folded on the treatment head (see below). Additionally or alternatively, the further material 3119 may form continuous stripes connecting consecutive pre-cursor blanks e.g. at both lateral perimeters of the side portions 3117.

FIG. 3A shows a preferred embodiment of the MD-orientation 3050 of an essentially unitary centre piece 3100 corresponding to the front-to-back orientation of the finished article. The pre-cursor blank 3000 may be supplied to the parallel treatment unit by any conventional means, such as guide rolls or bars, web support means such as transport belts, optionally equipped with web fixation means such as vacuum means etc.

The parallel treatment unit can be a conventional rotating essentially cylindrical drum, also referred to as a turret, and schematically depicted in FIG. 2A. The turret rotates around its longitudinal centre axis, and direction of rotation corresponds to the overall web transport direction, such that a web may be supplied to the turret tangentially, may be affixed to the outer surface of the cylindrical drum, and may after treatment and forming of the article be expelled from the turret about radially outwardly.

The turret may be in the form of a full cylinder, or may also be designed in a conventional manner by using rods, bars, or struts, such that a cross-section of the turret perpendicularly to the rotating axis may correspond to a polygon. Preferably, the turret comprises an even number of web treatment sections. These treatment sections comprise a treatment head, but may comprise further elements, such as further web support means (like vacuum belts), web guide means (like guide rolls), or web treatment means (like web cutting means).

Figure 2B:
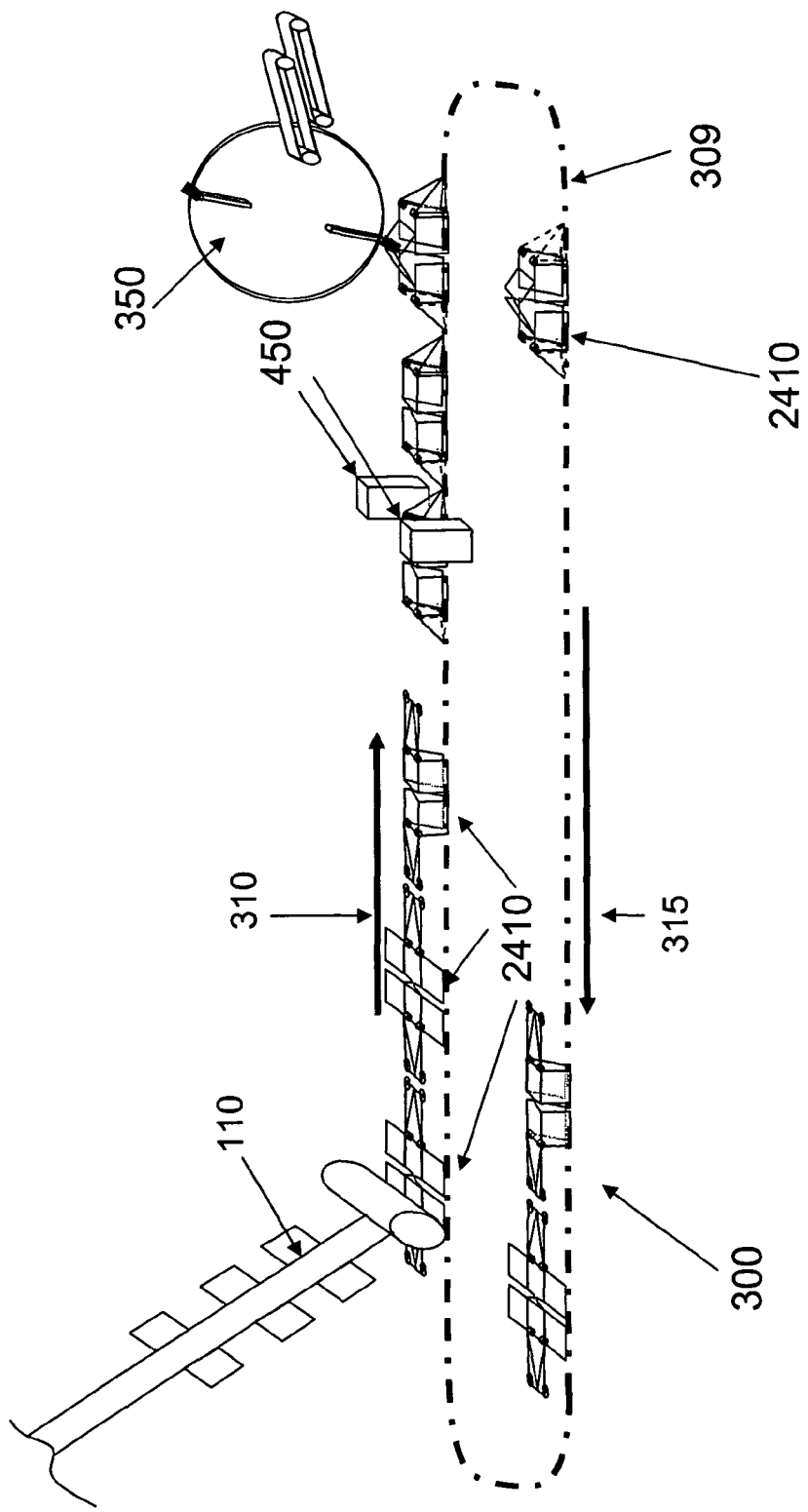

In an alternative embodiment, the parallel treatment unit can be an endless track guiding a number of web treatment sections, as schematically depicted in FIG. 2B, such as well known in principle from e.g. U.S. patent publication US-A-2002/084017. In such a design, the terms describing the positioning of e.g. the treatment head will need to be reformulated, e.g. "radially outwardly" will then correspond to "upwardly", "tangentially" will correspond to "parallel to the slide track", etc. As shown in FIG. 2B, a continuous series of pre-cursor blanks 110 is transferred to a corresponding series of treatment heads 2410, which are moved along a closed, or endless, track 309. The shown oval arrangement of such a track is preferred, as it allows straight and hence relatively easy arrangement of the various treatment tools interacting with the treatment head, respectively with the materials thereon. The oval form allows to use one essentially straight process track 310 and return track 315. The finished article 999 may be removed from the treatment head 2410 at the end of the process track by a removal unit 950 as described herein above.

Ad (B): Transferring the Pre-Cursor Blank 110 to the Parallel Treatment Unit 300;

The pre-cursor blank is transferred to the parallel treatment unit by conventional means, such as web support means 260, or web guide means 270. In case of the parallel treatment unit being a turret, the pre-cursor is essentially tangentially transferred to one of the treatment sections with the treatment head 2410. Before receiving the plus-shaped pre-cursor blank, the treatment head 2410 is in an upfolded configuration. This refers to a configuration, where the two longitudinally extending plates 2430, which can be pivotably connected to the centre plate 2420 such as by a hinge 2432, essentially form a continuous surface with the centre plate 2420. Essentially continuous refers to the fact, that, if the centre plate and the extension plates were plane, these would be straight aligned. If the centre plane is (e.g. cylindrically) shaped, there would be a smooth transition via an essentially 0° hinge angle. Instead of the hinged connection between the centre plate and the extensions plates, the latter may be affixed by different means e.g. to the frame of the treatment section, and may follow the movement by other means.

Ad (c): temporarily attaching the pre-cursor blank 110 to the outer surface 2422 of the treatment head, whereby the centre region 3115 is positioned on the centre plate 2420, and the front and rear regions (3112, 3118) to the longitudinal extension plates 2430 of the treatment head 2410. The attachment can be achieved by conventional means, such as vacuum.

In case the precursor blank is formed as a continuous web wherein the centre pieces of subsequent blanks are connected, these may be disconnected before they are attached to the treatment head, or on the treatment head.

The side regions 3117 of the precursor blank extend laterally outwardly of the centre plate 2420, optionally supported by lateral extension plates (not shown).

(d) Separating the Primary Web into Individual Pieces, Before or after Having Formed the Precursor Blank.

This separation of the primary web into a sequence of pieces may be performed at any time in the process before the material is folded, provided the then cut pieces may still be transported appropriately. The transport can be achieved by support means, such as vacuum belts, or by other continuous webs connecting subsequent pieces. (see optional process step (j). In a preferred execution, the blanks are separated at the time they are transferred to the treatment head on the turret. The separation can be performed by any suitable conventional means, such as by rotating blades, laser cutting, etc.

Ad (e) Pivoting the Longitudinal Extension Plates Downwardly in the Direction Towards the Centre of the Rotating Drum;

The front and rear regions of the blank as initially supported by the longitudinal extension plates can readily be folded downwardly by pivoting these plates, e.g. at an angle of about 90° to the centre plate.

Ad (f) Folding the Side Portions 3117 of the Pre-Cursor Web 110 Downwardly, Optionally Employing Guide Means or Downwardly Foldable Lateral Support Plates;

The side portions 3117 may either be supported by corresponding laterally extending support plates, which may be also pivotably affixed to the centre plate, and which may be then pivoted downwardly.

Alternatively, the side portions may be supported by alternative guide means such as stationary guide plates which may be affixed to a base of the turret (and hence do not rotate), and at the appropriate position these support means terminate so as to allow the sideways extension to be folded downwardly, such as by being pulled downwardly by the appropriately connected waist hoop material towards the centre of the turret. If these stripes of optionally elasticated and extended materials are connecting consecutive blanks (i.e. if these are not yet disconnected or cut) they will by nature of the curvature of the path on the turret, automatically pull the side panels appropriately downwards, thus not necessitating a support plate or guide means.

The downward folding of the lateral portions of the centre region 3115 of the Plus-shaped blank 110 occurs along a curve-linear folding line 3300 as indicated in FIGS. 3A and C will create a bulging of the centre region, thereby forming a cup-shaped structure in the finished article 999 reflecting bodyshaped contours during use, as described in more detail in co-pending patent application PCT/EP06/002166. This bulging may optionally be eased by appropriately shaping the outwardly facing surface 2422 of the centre plate of the treatment head, and by respective creases in the side areas of the centre region.

Ad (g): Connecting Respectively Adjacently Positioned Side Margins;

After the front (3112) and rear (3118) regions as well as the side portions 3117 of the Plus shaped pre-cursor blank have been folded downwardly, the side-margins of respectively adjacently positioned extension regions are positioned to allow respective connecting to form a closed structure (refer to FIGS. 3 A and C), i.e. side margins 3113 of the front region 3112 will be positioned adjacent to the forward margins 3116 of the side portions, and the side portions 3123 of the rear region 3118 will be positioned adjacent to the rearward margins 3126 of the side portions.

In the simple arrangement as shown in FIG. 3 of the blank forming a Plus-shape with the arms being essentially rectangularly arranged, the folding steps along essentially perpendicularly arranged folding lines will bend these arms out of the original plane of the blank and arrange cross-directionally oriented edges adjacent to longitudinally oriented edges, such that the subsequent step of connecting these to each other will then fix the 3D-shape of the article. Thus, by the simple downward folding and subsequent connecting, complex structures may be formed, and edges extending essentially perpendicularly on the (flat/plus-sign shaped) blank can now be connected to each other. The order of the downward folding of the side portions relative to the front and/or rear regions depends on the desired design, e.g. this defines which region or portion will overlap the other. Insofar, the order of the steps as described and claimed herein does not necessarily define the chronological order.

The connecting can be achieved by various conventional techniques such as described in more detail in the above references co-pending application PCT/EP06/002165, e.g. by applying adhesives and subsequent compressing, or by using heat, or ultrasonic energy or the like, or by joining the male and female components of mechanical fasteners to each other under slight pressure. Depending on the type of connecting, some or all of the web materials may project beyond the respective edges of the support means. There can be one or more sets of treatment tools interacting with the treatment head. The connecting tools may comprise an active and a passive element, such as an (active) pressing tool, and the passive anvil. Treatment tools may be affixed rotatingly to the same axis as the turret, or to an axis essentially perpendicular to the axis of the turret, such that the turret segments (and hence treatment head) pass rotatingly.

The present invention provides a wide flexibility for selecting the connecting means and tool, in particular as it allows two sided working on the bonding, as the materials overlay the treatment head and may then be treated by one or more corresponding treatment tools, which may interact with the treatment head in any way.

Ad (h) Optionally Further Treating the Article;

After the downward folding of the extensions, the basic form of the article is defined and fixed by the connecting. A particular useful further step is the combination with a further web material forming a hoop 3119, thusly also stabilizing e.g. the unsupported side portions as described under point (g), if the pre-cursor blank 110 does not already comprise such a material. Also, further connecting means may be added, e.g. reuseable closures, and the like, or certain parts may be specifically treated, such a by being mechanically treated to impart different mechanical properties, or the surfaces, preferably oriented towards the wearer during use, may be treated with lotions, creams, or the like, for improved skin friendliness or purposes of therapeutic treatment.

Ad (i) Removing the Article from the Web Handling Equipment.

Once all appropriate operations are performed on the now shaped article, this may be removed from the turret, by employing various means, such as may be vacuum suction, air pressure, and the like.

A particularly suitable way is further shown in FIG. 2A, showing a rotating disk 950 positioned adjacent the turret 300 and comprising radially moveable fingers 960 arranged to engage into the treatment head 2410 and the leg openings 3130 of the article, so as to allow pulling out of the formed article 999 upon further rotation of the turret 300 and the rotating finger disk 950. One of such disks may be positioned on each side of the turret. Web support means 260 may further transport the formed article 999, such as to a packaging station (not shown). Care should be taken during this step to not unduly press or deform the resulting product, as it may form a "3D-Article", which might not be foldable flat with all seams also laying flat on a plane, but which might crumple during this step.

In addition to the just described process steps, the process may further include other process steps, in particular step (j) adding a further material to the pre-cursor blank.

Figure 3C:
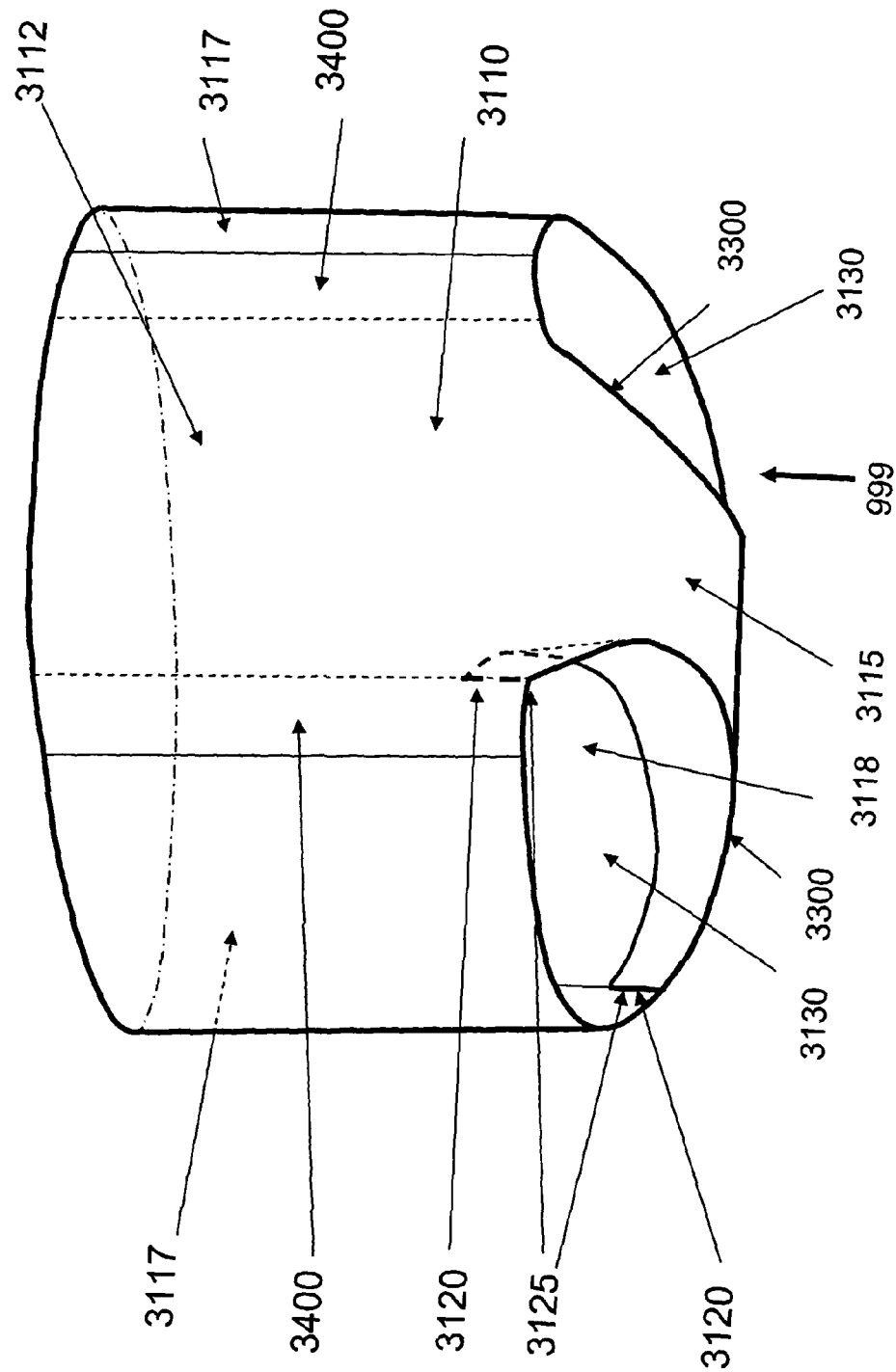
Figure 3E:
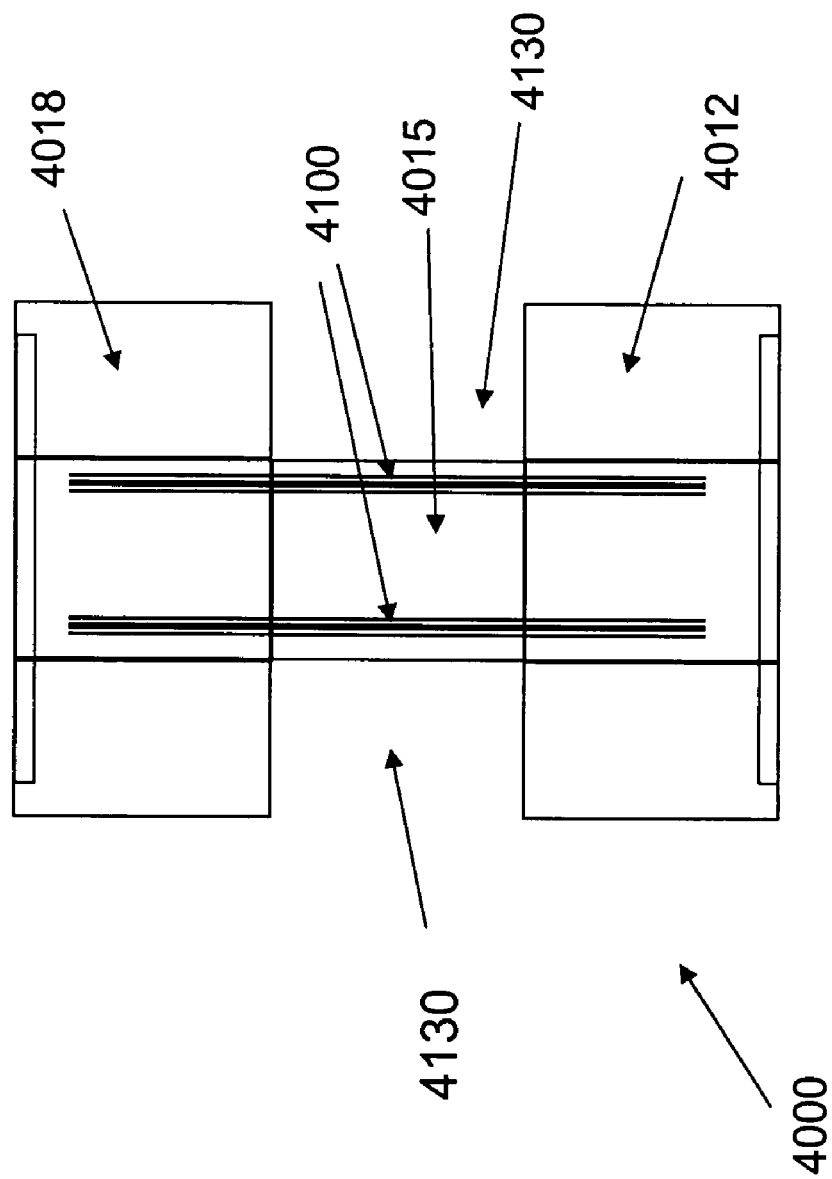

In particular, such a material may be a waistband material 3119, as depicted in FIGS. 3A and 3C, which may be added from a supply roll 2210 as web material 2100 as shown in FIG. 2A. Such a material may also be pre-combined with another further material, as described herein below, when a leg cuff material is pre-combined with a side portion material, and the combined material is then added to the centre piece (refer to FIG. 5 A to D).

The present invention also relates to products as may be manufactured by the manufacturing methods as described herein, and which are distinctly and beneficially different to typical conventional designs having a shape, that, when the article is cut open along lines extending longitudinally through the side portions of the article and laid on a flat surface, being narrower in the crotch region of the article than in the waist region(s). Such articles are often also referred to as "hourglass shaped" articles 4000 (see FIG. 3E—showing front (4012), rear (4018) and centre (4015). It should be noted, that typically such designs comprise elastic sealing elements 4100, such as well known leg elastics and/or elasticated barrier cuffs, which run from the front to the rear along the crotch crease of the wearer during use. Thus, these elements will unavoidably create a force, upon which the article will "sag" or be pulled downwards (on a standing wearer).

In contrast, articles according to the present invention and as may be produced by the above described process comprise a primary or centre piece web material to which laterally outwardly extending side portions are attached and later connected, such that this pre-cursor material forms a Plus-shape—refer to FIG. 3. The outwardly extending portions are only partly attached to the centre web at the inwardly oriented front and rear corners (refer to FIG. 3A to D), and loosely overlay the centre web between these connecting points. Upon the folding and connecting of the respective regions, these overlay regions correspond to the leg openings 3130 of the article.

If the article comprises elasticated elements such as to perform a sealing function in the case of liquid absorbent articles, these may be positioned circumferentially around the waist and/or the leg of the wearer, and thus will not induce the "sag" as described for conventional hourglass shaped articles.

The side portions of the pre-cursor blank may also be referred to as hip/thigh panels in a finished article 999, as these—in contrast to conventional side or hip panels—not only cover the hip of the wearer during use but extend further down to the thighs of the wearer. Thus, the present invention provides articles with a closed structure encircling the legs of a wearer, which may also referred to as a leg hoop. Such a leg hoop may be formed of a section of the hip/thigh panel and the laterally outward section of the centre region, as delimited from the remainder of the centre region, which may be referred to as centre crotch region, by the curvelinear fold line 3300, as depicted in FIG. 3D. Alternatively, as shown in FIG. 3C, a further material may be connected to the crotch region along a curvelinear connecting line, or a connecting region delimited by a curve, which may be further connected to the hip/thigh panel and thus form the leg hoop or cuff.

Typically, the resulting article cannot be laid flat on a flat surface with all connecting lines or regions also being laid flat on the plane, but which can be laid flat upon cutting open connecting lines (or borders of connecting regions), then forming a plus-sign (or cross) shape blank.

Whilst the above description aimed at explaining the present invention in simple terms, there are a number of particular embodiments for the process and the finished product, some of which are described herein below. However, these embodiments should not be seen in any way limiting the scope of the invention. It should also be noted, that the following executions can be combined.

In one particular execution, the present process allows the manufacture of articles wherein a leg hoop is formed by the side portion material 3117 encircling the outer hip and thigh of the wearer and by a further inner leg cuff material, as schematically depicted in FIG. 4, showing a perspective view of such an article.

Figure 5B:
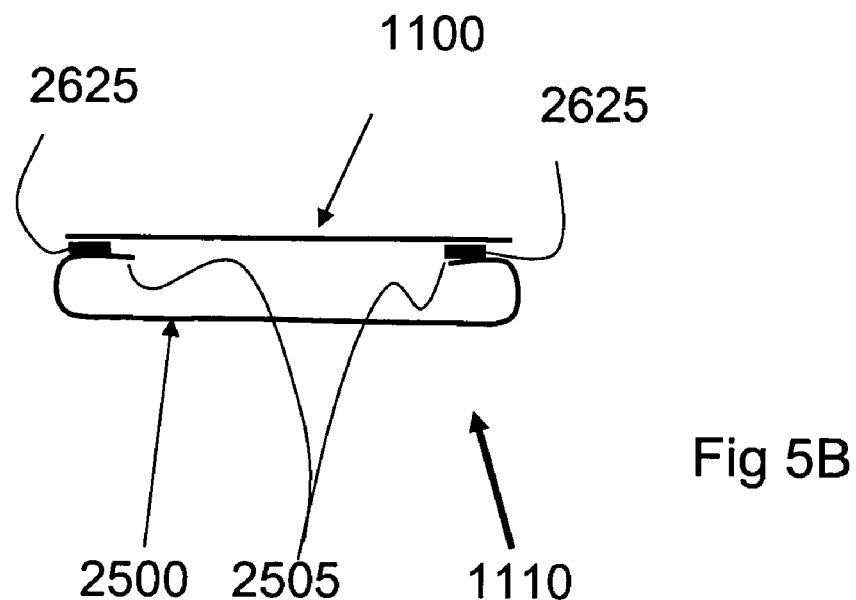
FIGS. 5 A and C—depict schematically a process set up to form a Plus-Shaped pre-cursor blank.
Figure 5D:
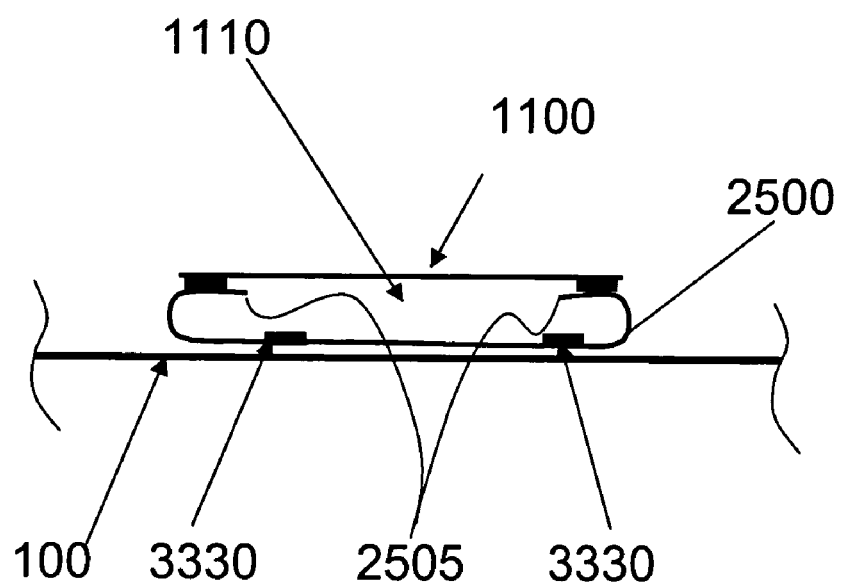

The making of the pre-cursor blank is further explained by referring to FIG. 5, depicting schematically the process steps to arrive at such a design, within the overall process lay out as shown in FIG. 2A. To this end, a side portion material 1100, running along the MD direction 3050 aligned with the MD direction of the Plus-shaped pre-cursor, is combined with pieces of a leg cuff forming material 2500. This cuff forming material 2500 runs initially parallel to the side portion material and is longitudinally downwardly folded by 180° on a folding station, indicated at the position 2600, to a predetermined width of overlap. Thus after the folding station, the perimeter 2505 of the material is indicated by the dashed line. This web is then run over a 45° turning bar or roll 2610, inverting the web, such that the perimeter 2505 becomes visible. The upwardly facing folded region 2625 can now be treated such as by applying glue by a glue applicator 2620. This web is now cut by a cutting unit 2630 to the appropriate length for forming the height of the leg hoop, and attached with the glue treated folded regions to the side portion material, as depicted in FIG. 5A. Commercially available tape cutting units equipped with a rotating head and a side-fed windowed anvil may be employed for this cutting operation. The receiving web 1100 may be slightly moved downwards by the rotating cutting head, and pressed against the glue treated folded region of web 2505, thereby overlapping respective regions and closing the leg hoops. FIG. 5B shows a schematic cross-sectional view of this combination 1110 of the side portion 1100 with a leg hoop material (2500) attached thereto and after being separated from the continuous web 1100, e.g. by a cutting tool 2640, cut to the appropriate length. This cutting may be achieved simultaneously with transferring the combined material 1110 to the continuous centre piece material 100 (ref. to FIG. 5C). There, it may be attached by means of a curve-linear connecting line 3300, e.g. a glue line. FIG. 5D shows a schematic cross-sectional view through this composite. As further shown in FIG. 5C, the process may include the addition of yet a further material 2100, which will form a waistband hoop in the finished article. This material may be supplied over conventional guide and/or support means, and may be attached to the side portion material, here shown as being attached to the lateral outward side margins of the side portion material. When the thusly described process is mirrored for a second side portion, the Plus-shaped blank 110 is finalized, and may be transferred to the turret, before or on which consecutive blanks are separated along the separation line 111.

A further particular execution of the present invention relates to article designs, where the centre piece extends longer in the MD-direction than the extensible web-material 2100, which will form the waist hoop 3119 in the article, even when this is at least partially extended (see waist hoop material 2100 in FIG. 5C). In one execution, the waist material 2100 may be extendend, preferably elastically extended, so as to match the length of the centre piece 3100. In another execution, an extra length of waist web material may be metered in, such that the waist material can be extended to the desired level, the extra length of (surplus) waist material forming an overlap in the front and back parts of the waist hoop, or the extra length of waist material being removed when the left and right waist hoop portions are joined. In addition or alternatively, the centre pieces of subsequent blanks may be separated, and separated end regions may be positioned in a partly overlapping arrangement ("shingling") before the waist material is added to the blank.

Figure 6A:
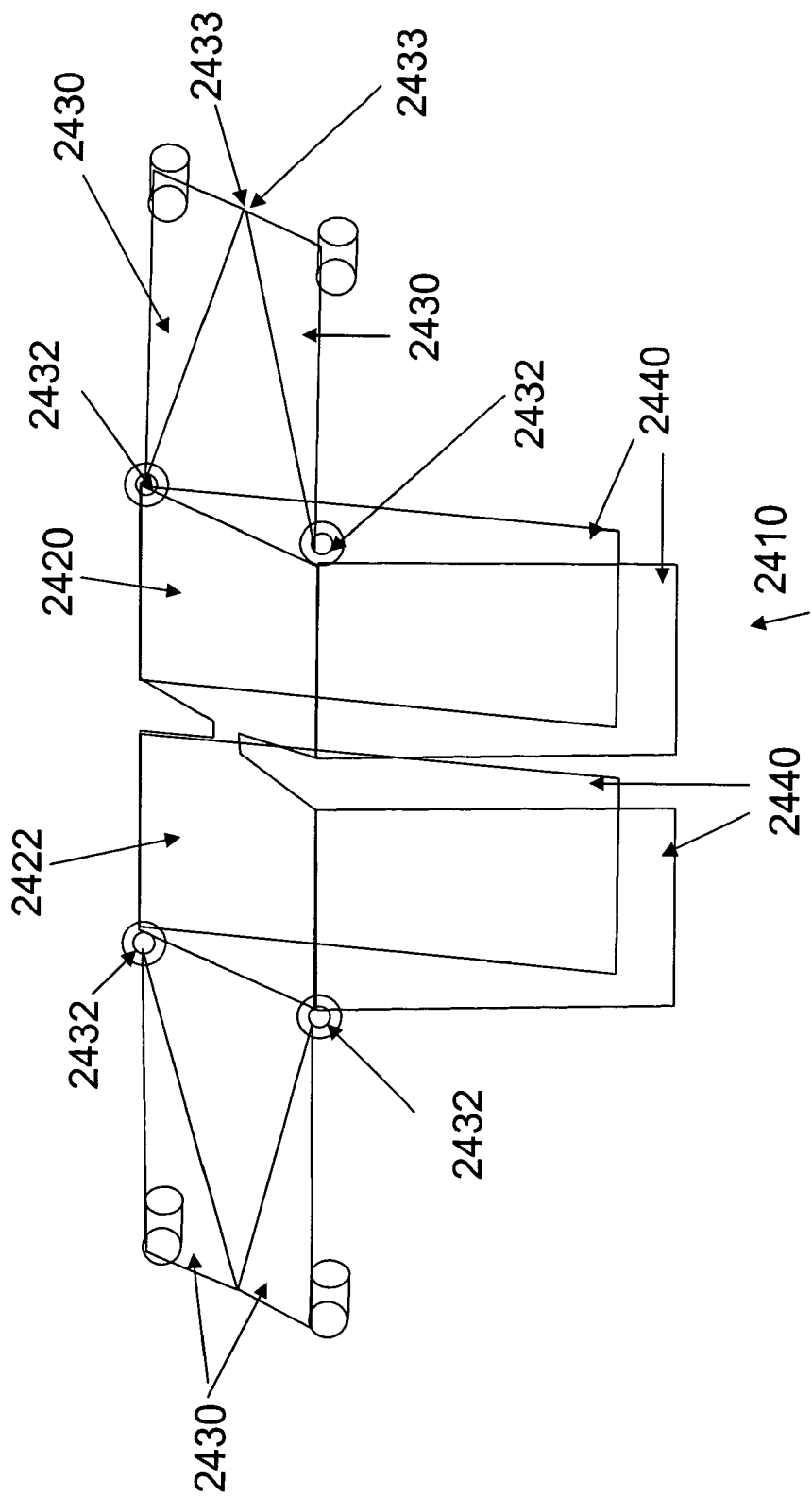
FIGS. 6 A and B show a schematic view of a treatment head.
Figure 6B:
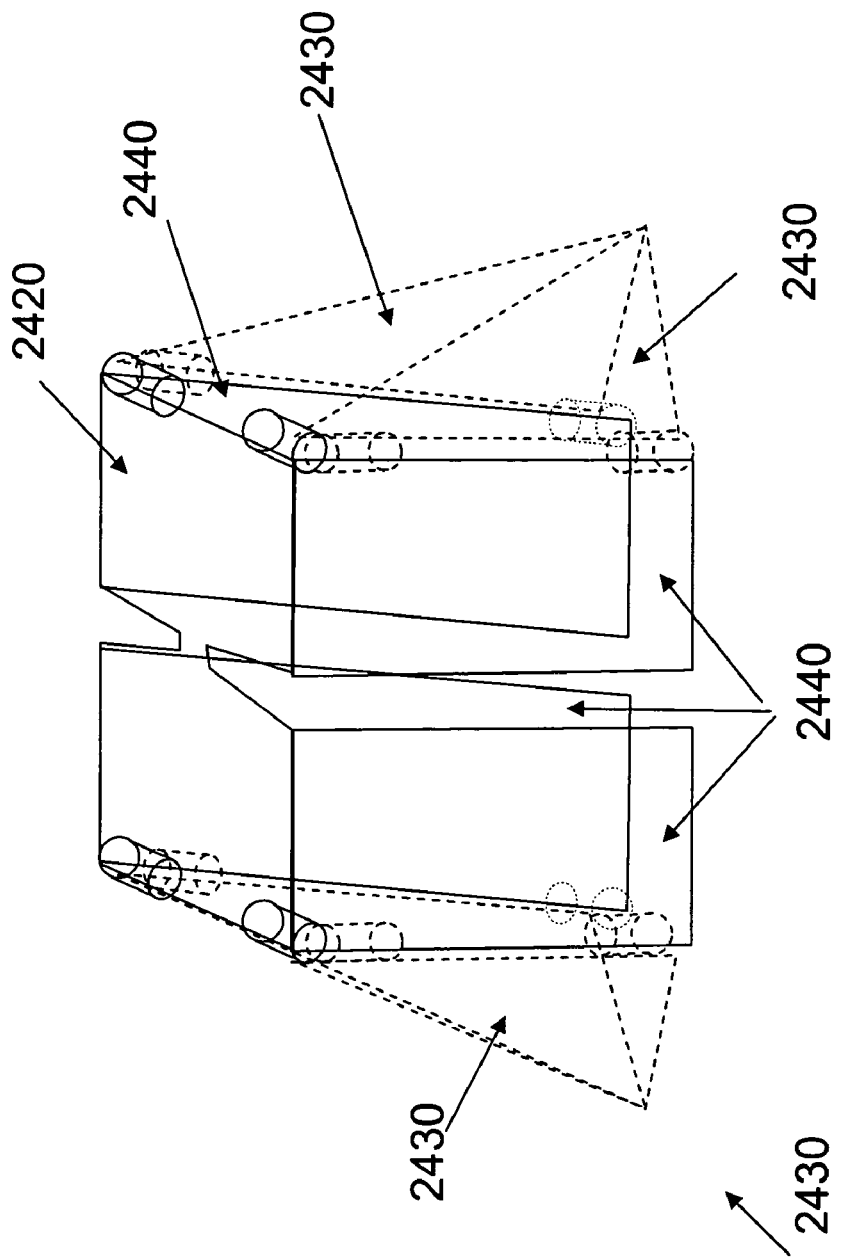

When forming an article without a separate web material forming the waist hoop in the finished article (i.e. such as shown in FIG. 3), the front- and rear regions of the centre piece and the side pieces can readily be folded downwardly on the forming head (refer to step (e) in the above description). In case of a web material, which is intended to form the waist hoop in the finished article is already attached to the lateral perimeter of the side regions, a particularly useful design of the forming head 2410 may be used. Therein, each of the longitudinal extension plates 2430 may consist of two sub-plates, e.g. in a triangular shape, as depicted in FIG. 6A. Simultaneous with the downward folding, the plates also rotate around the bi-directional hinge point 2432, such that the medial corners 2433 or the front extensions are oriented at about 45° forward and inwardly, as depicted in FIG. 6B. The pivoting as well as the rotation may be achieved by conventional means, such as cam systems, pneumatic or electric systems, spring loaded systems, or servo motors. As shown in FIG. 6, the lateral extension plates 2440 of the treatment head, are downwardly affixed by somewhat more than 90°, e.g. by 100°, such that the now downwardly oriented peripheral ends are positioned at a smaller CD distance than the CD width of the centre plate. As shown in FIG. 6A, this may be achieved by sideways extension plates, which may or may not be pivotable, but which are narrower at the lower end than at their upper end, and against which the side panel materials may be pressed. This execution will allow easy connecting respectively closing of the waist material, e.g. by heat or glue pressing against the extension plates, essentially concurrently with the cutting thereof near the medial corners 2433.

A further particular execution within the scope of the present invention relates to the positioning of the hinge-points 2432 of the longitudinal extension plates. As these hinge points are typically arranged below (e.g. towards the centre of the turret) the surface of the centre plate 2420, the downward folding will create an extension of the web material in its MD direction. This may be compensated by the elastic properties of the web. Alternatively, the hinge-points may be affixed moveably along the MD-direction relative to the extension plates, thusly compensating the extension of the web. Such designs are well known to a skilled person, refer e.g. to EP-A-0717972.

The downward folding of the front and rear regions and the side portions (i.e. the steps d) and e) as described hereinabove) may be executed simultaneously or one after the other, thereby defining if and how the individual panels overlap. Depending on the intended design, the front region material may overlap the outside of the hip/thigh panel (relative to a wearer being "inside"), as shown in FIG. 3, or—conversely— the hip/thigh panel may overlap the front region, as shown in FIG. 4. Similarly, a piece of material in the front or rear region adjacent to the cut 3125 (refer to FIG. 3B) may be folded and connected inwardly or outwardly, or it may be cut away.

Further particular considerations relate to the centre region web piece, which may be a continuous, unitary piece of material, or which may be—prior to be transferred to the treatment head—composed of several pieces of material connected to each other so as to form the centre piece. For example, the rear region may comprise an elastic material, or it may be at least extensible in the MD direction, so as to remain body conforming during use.

Similarly, the side portions 3117 forming the hip/thigh panels may be composed of different materials, or may be composed of one material, which may have sub-regions with different properties, which may, for example, be induced by a treating these regions differently, such as mechanically or thermally.

This allows to design very cost effective yet very well fitting articles, as—for example—relatively expensive elastication can be limited to regions where required, but other regions may be inelastic, or elasticized to a lesser degree. As an example, the elastic contractive force may be desired to be at a higher level in the waist region, lower in the hip regions, and higher again in the leg region. Also, the higher contractive forces may be achieved by varying degrees of pressure on the wearer, for example, in the waist region, the forces may be spread over a smaller area (thus creating higher pressure on the body), whilst for the leg hoops, a larger area resulting in lower pressure may be used to apply these forces. If desired, areas of the hip/thigh panel can also be coated with materials raising the coefficient of friction to the skin, thus providing good fit of the product with minimum surface pressure on the skin.

Further, because of the specific bending and folding in the process, materials, which are delivered in machine direction, may be applied in the article such that their original MD direction extends now cross-directionally to the orientation of the article. This will—for example—allow to use elastic material more efficiently, as MD-oriented stretch is much easier and more cost effective to induce to a material than CD-oriented stretch.

Figure 7:
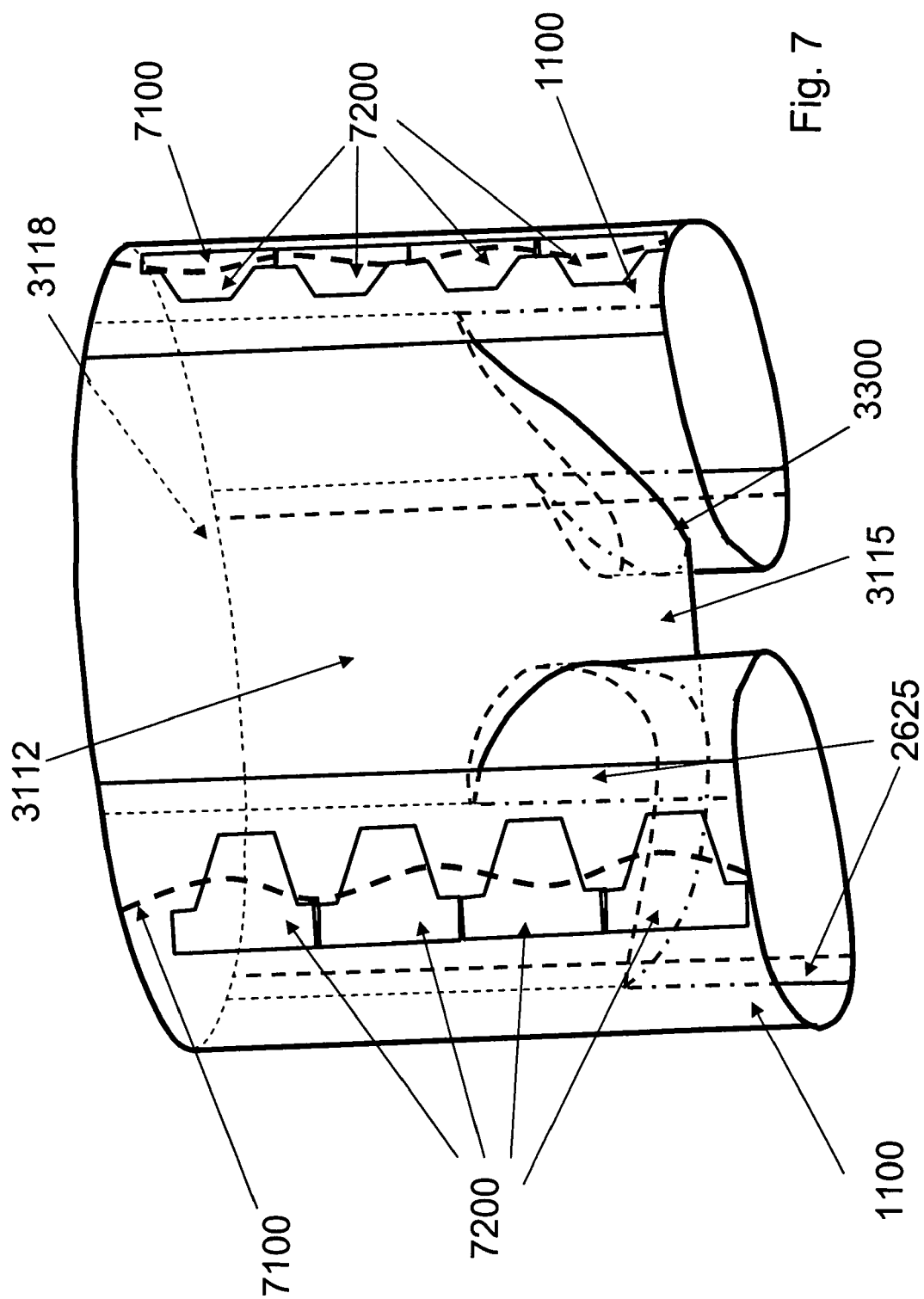
FIG. 7—shows a perspective view of a further article according to the present invention.

In addition to connecting regions permanently, such as adhesively or thermally, the present invention allows to produce articles comprising a hoop, e.g. a waist hoop in a pant like article, which may be connected by means of mechanical fasteners, glue or thermal bonds, or macro fasteners in the front and/or rear regions rather than in the sidepanel regions, such as depicted in FIG. 7, showing an article as of FIG. 4, additionally comprising a predetermined tear line 7100 in each hip/thigh regions. This tear line 7100 may be created in the side portion material 1100 (ref. also to FIG. 5A), prior to the addition of the leg hoop material 2500. Such a tear line may be created by partial perforation, so as to allow a user e.g. to inspect an article. In case it is decided to continue the use of the article, it may be closed again by the secondary closure means, here shown in form of mechanical fasteners 7200, designed to engage e.g. with the side portion material, respectively with the hip/thigh panel.

Such recloseable connecting means may further be employed in combination with permanent connection means, such as glue lines. Then, the re-closeable means may be used in addition, e.g. to adjust the size, or they may replace the permanent ones, once these are destructively opened, but the article may be otherwise suitable for further use. The re-fastenability may also be designed such that the article may be fully opened before being applied to a wearer, optionally in a further process step, but preferably by a caregiver. Then, the line 7100 may fully separate the material, which is then held together by the re-closable connecting means 7200, e.g. mechanical fastener hooks. This design allows to apply the article in a conventional manner as currently applied for baby diapers.

Figure 8A:
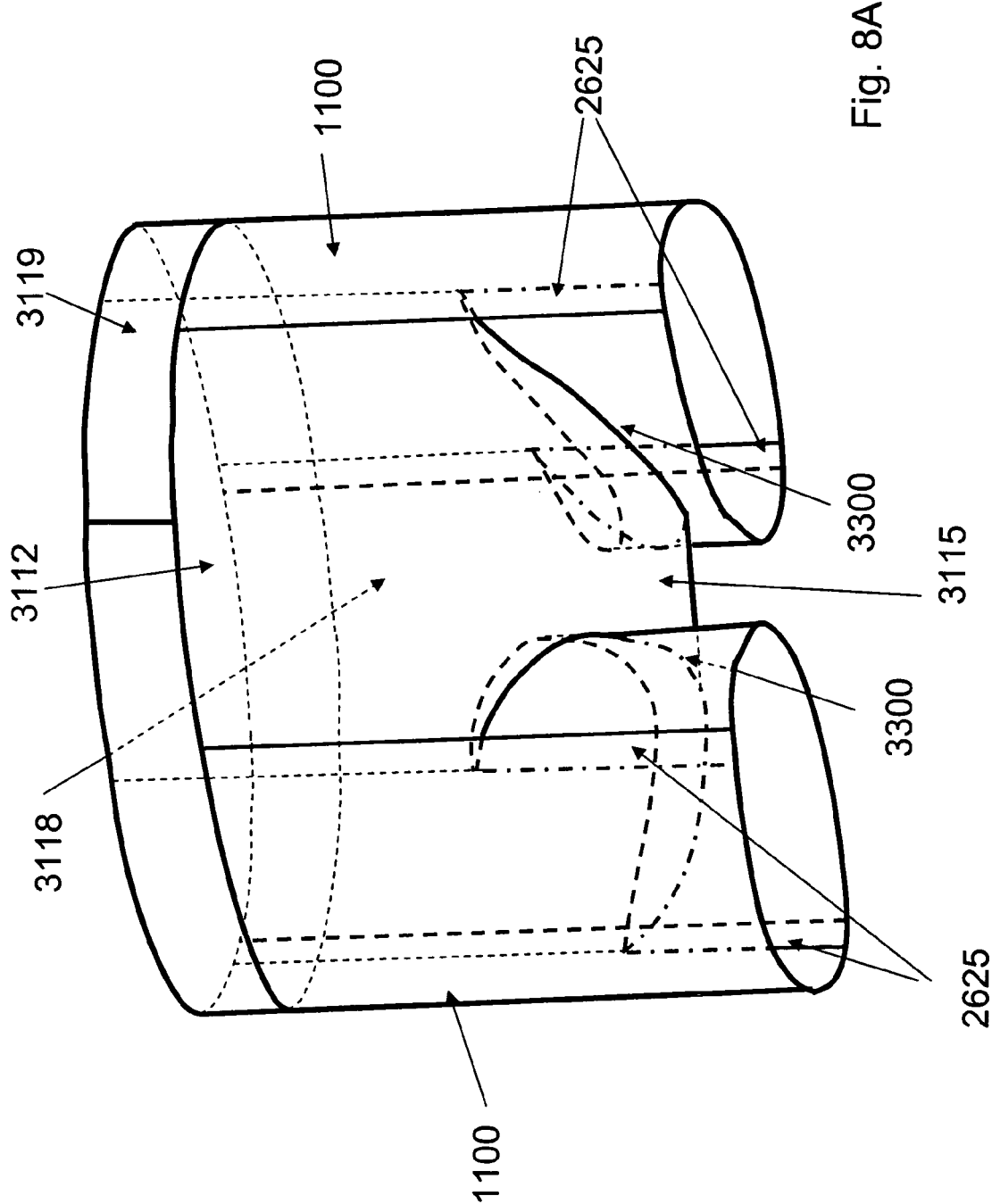
FIGS. 8 A and B show perspective views of further articles according to the present invention.
FIGS. 8D and E show schematic views of an article according to the present invention comprising a drawstring waist feature.

The present invention allows particular flexibility in the design of the waist features of an article. Conventional industrial manufacturing processes did not allow waist features— such as waist shields, or waist bands—to be connected or even interrupted in the front or back region of the article, as schematically depicted in FIG. 4, showing a waist hoop 3119 closed by two connections in the front and the rear of the wearer respectively, and further in FIG. 8A, showing a waist hoop 8119 connected only in the front region of the wearer. FIG. 8B shows an interrupted hoop, with two gaps 7400, one in the front region and one in the back region of the wearer. This is in contrast to conventional high speed produced articles, where the seam in the waist feature had to be positioned in the side or hip regions of the wearer, refer to FIG. 8C, showing a training pant 1000, connected by side seams 1010, and a waist element 1015, which is also connected at the sides.

A particular waist feature is schematically depicted in FIG. 8D. It may comprise two pieces of elasticated waist belt material 3119, each connected with one end only along a connecting region or line 7300 to the region of the hip/thigh panel 3117 overlapping the rear region 3118 of the centre piece, respectively connected to the hip/thigh panel in the proximity of the connection to the rear region of the centre piece. The pieces may then be loosely held like a draw string in an envelope, e.g. formed by back folded extensions of the hip/thigh panels, in the figures indicated by the foldover perimeter 7500. The draw strings may be re-closeably connected to each other in the front region 3112 of the centre piece, or each may be connected to the front region 3112 directly. In a preferred embodiment, this may be achieved by the use of mechanical fastening means 7200. This design allows, e.g. the caregiver, to readily adjust the waist circumference of the article to the user, as indicated in FIG. 8E, showing the same article as in FIG. 8D, but with the drawstring pulled closer, thusly having a smaller gap width 7400', e.g. adapted for a smaller waist circumference. The drawstring material may be an essentially unitary material, and may be at least in certain regions elastic. It may be composed of various materials, e.g. being elasticated in the regions corresponding to the hip regions, and being non-elastic, e.g. a conventional non-woven or non-woven film laminate, in the closure region. Typically, it will be made of a web material, e.g. in form of a band, which for comfort reasons has preferably a width of more than about 1 mm but less than about 120 mm. During manufacturing, the drawstring may advantageously be connected to the side portion material, before this is connected to the centre piece to form the Plus-shaped blank. At that time, it may also be enveloped by the side portion material being folded over. The folded material may be trimmed at the front end, so as to allow easier access to the waist material during the process or upon use. The drawstring material may already comprise mechanical fasteners in its front portion. Such mechanical fastener may have a unidirectional engagement functionality, such that they can be readily dis-engaged if pulled forwardly (e.g. during the process or by the caregiver), but they strongly engage if strained along the other orientation.

This drawstring design principles may evenly be applied to leg hoops, i.e. they may each comprise one piece of elasticated leg hoop material, connected with one end only to the region of the hip/thigh panel overlapping the rear region of the centre piece, respectively connected to the hip/thigh panel in the proximity of the connection to the rear region of the centre piece. The piece may then be loosely held like a draw string in an envelope, e.g. formed by back folded extensions of the hip/thigh panels, and may be re-closeably connected to the centre piece, or directly to the inner leg cuff piece.

Yet a further embodiment showing a particular advantage of the present invention relates to an article comprising a so called secondary topsheet, as well known in disposable absorbent articles, such as baby diapers. Such materials, typically light-weight non-woven materials, are positioned between a (first) topsheet overlaying the core, e.g. the absorbent core, and the skin of the wearer, and they are supposed to allow faecal material to pass through an opening therein, which is in registry with the anal opening of the wearer. Then, the secondary topsheet either masks the faecal material and/or prevents it from contacting wearer's skin. However, all conventional designs, as shown e.g. in WO 03/009795, do not adequately support the tasks of (i) keeping the secondary topsheet in contact with the skin of the wearer whilst keeping the opening (ii) sufficiently open and (iii) in registry with the anal opening to allow the faecal material to pass through, as well as (iv) providing the void space required to take on and store the faecal material. The present invention provides a particularly suitable design, as schematically depicted in FIG. 9, overcoming such disadvantages as well as a simple process for the manufacturing thereof, as further explained in reference to FIG. 10 A to G.

In its simplest form, the secondary topsheet 9100 may be of any material suitable for this purpose, such as conventional non-woven materials, not needing any elastic properties. The opening for being positioned in the region of the anal opening of a wearer during use has a MD and a CD extension and a respective perimeter at least during use. The article may further comprise at least two elastic elements extended to a predetermined extension, each connected to at least a point of the perimeter or in proximity of the perimeter of the opening, whereby each two connection points are in an opposing position relative to the centre of the opening, and at least to a connection point of the topsheet or the secondary topsheet, the point being positioned outwardly away relative to the centre point of the opening, thereby creating a force to sustain the opening. In a specific embodiment, the secondary topsheet comprises a cross-directional cut line so as to form the opening positioned in the region of the anal opening of the wearer during use, wherein the elastic elements, preferably elastic threads or bands are positioned essentially aligned with the longitudinal centre line of the article. Further, the elastic elements are connected to a point on the perimeter of the cut line or to a point in the proximity of the cut line and to a point longitudinally away from the cut line, preferably in the waist region of the article, such that the tensioning of the elastic elements sustains the opening formed by the cut line.

Figure 9:
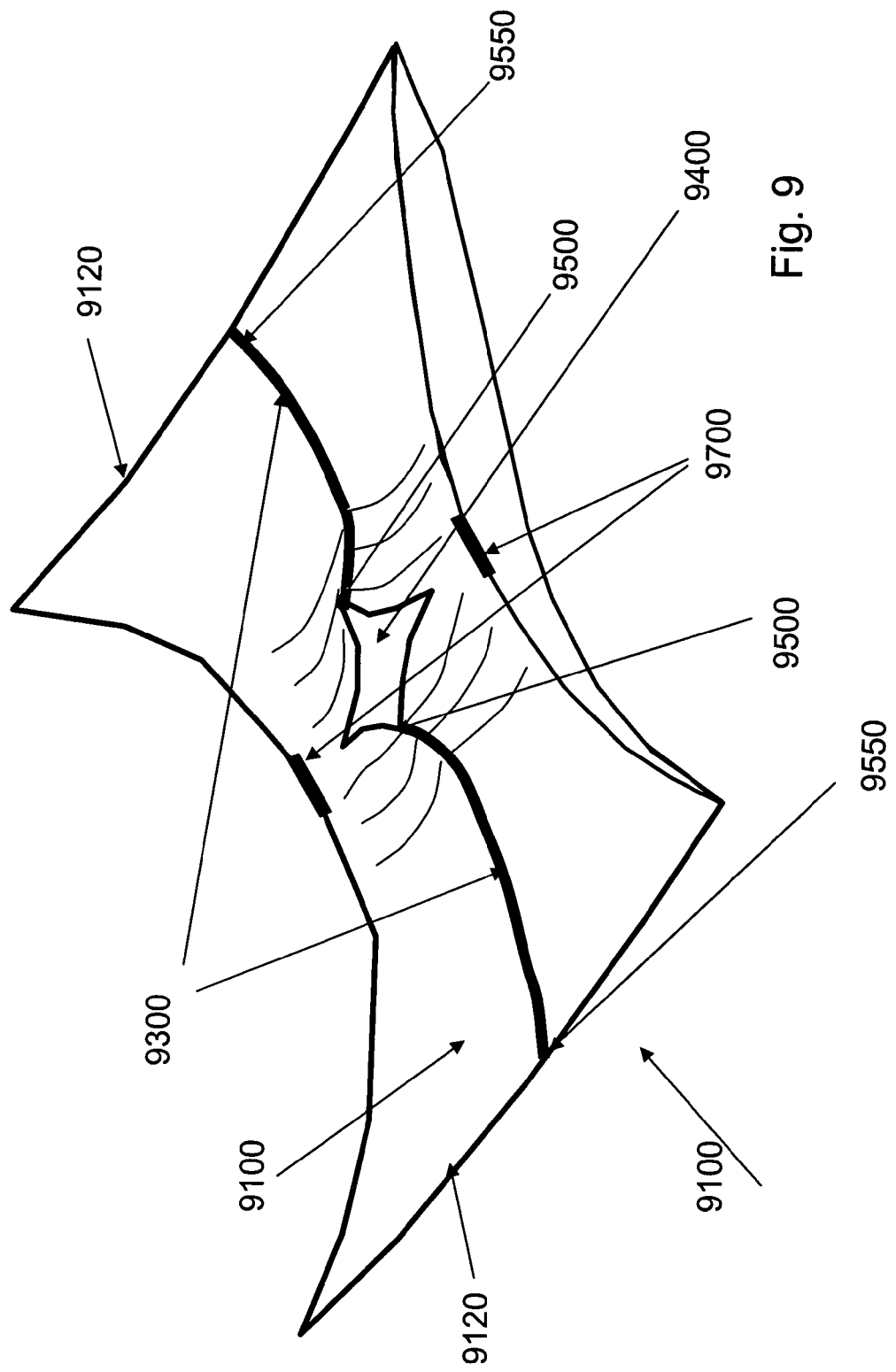
FIG. 9—shows a schematic perspective view of a secondary topsheet with an aperture.

As depicted in FIGS. 9 and 10, the elastics are positioned along the longitudinal centre line of the web, respectively of the article 3050. The elastic can readily be extended to a predetermined extension, and should be connected to the secondary topsheet material at least at a point 9500 at the perimeter of the opening, respectively a cut 9400, which may then form the opening. The elastic material is further connected at least to two further points 9550 longitudinally offset. This web may then be apertured, such as by being cross-directionally cut at a width corresponding to the desired opening width at a position corresponding to the anal opening of the wearer during use. Then the elastic material 9300 will create the appropriate forces to maintain the opening 9400. In one exemplarily described manufacturing process, the elastic 9300 is first combined to the web material, and this composite, preferably trimmed to an hourglass shape, as indicated in FIG. 10A, is added to the centre piece 3100 of the pre-cursor blank on the surface opposite to the one where the side portions are or are to be connected, corresponding to the inner side of the article after folding. The cross-directional cut may be introduced at that point in time, or preferably before combining the composite to the centre piece.

The secondary topsheet is connected to the pre-cursor blank 3100 at its front and rear perimeter along connecting lines 9120, which may be any conventional connecting means, preferably fine glue lines (see FIGS. 10 A and D). In a second step, the centre piece 3100 with the secondary topsheet 9100 is longitudinally folded along fold lines 9600, such that the secondary topsheet is not folded in the narrower centre region, but rather in wider front and rear regions. This fold, as shown in FIGS. 10B and B will overlay the outer parts of the secondary topsheet. The secondary topsheet can now be connected to the edge of the centre piece, as indicated as bond line 9700 in FIG. 10F, but only in a region corresponding to the region of the cut towards the anal opening. Now, the z-fold can be removed, leaving the parts of the cuffs attached to the secondary top sheet, and the front and rear parts of the cuffs to the hip/leg panel, thereby exposing parts of both surfaces of the cuffs at the same time. Now, the precursor blank, as depicted in FIGS. 10C and G, may be transferred for further processing.

During use, the secondary topsheet will be held closely to the skin of the wearer, and the opening will be maintained open in longitudinal direction by the contractive forces of the elastic. Furthermore, it will be maintained open cross-directionally because of the connection to the side margins of the centre piece, now being upwardly folded towards the crotch crease of the wearer, thereby providing the void space required.

In an alternative execution, the elastic may be applied cross-directionally in the article, whilst the cut to create the opening is applied perpendicularly thereto. In yet a further alternative, the opening may already be created by cutting out a piece of the secondary topsheet material, and elastics at any orientation may be applied to maintain the opening in place. In yet a further alternative, the secondary topsheet may be made of a material exhibiting in itself elastic properties, or it may be a composite of such a material and other non-elastic materials.

In a preferred embodiment, the secondary topsheet material may be particularly treated to enhance liquid penetration in certain regions, e.g. regions intended for receiving aqueous exudates, such as urine, whilst other regions, such as the regions surrounding the opening, are treated to prevent e.g. faeces to penetrate through.

A further preferred execution of a secondary topsheet includes means for enhancing skin friendliness, such as by being highly air permeable, or by comprising particularly skin friendly substances, such as cream or lotions.

A further particular design feature relates to articles, such as pant-style articles, which may, for example fit lower in the front of the wearer than in the back. Such products can be readily achieved by shaping the hip/thigh panels not rectangularly, but, for example, trapezoidal, and the front and rear region of the centre piece will also have a corresponding difference in length.

Whilst the present discussion focused of the forming of the article from essentially flat web materials, each of these materials may be a composite, made partly or fully of several layers of web materials. In particular, for the application as an absorbent article, an absorbent core may be inserted, which may be also an essentially web-like material, or a sheet, or which may be in a three-dimensional shape itself, or which may comprise an acquisition system comprising at least one extra layer of material with high strike through performance"

The present invention may be applied to a wide variety of articles. Without wishing to imply any limitation, it may be used for the making of disposable absorbent articles, such as baby diapers design, where the connecting of the front region to the hip/leg panel is achieved by recloseable means, such as mechanical fastening means, or tapes, pre-closed pants and training pants, menstrual pants, adult incontinence articles and the like; of disposable articles as such, such as disposable underwear; of non-disposable articles, such as underwear, swimwear, etc.

Similarly, the present invention covers the articles as produced by the present invention, as well as particular embodiments of articles, which hitherto have not been able to be manufactured in industrial scale on high speed production machinery.

The invention claimed is:

1. A method for manufacturing shaped articles, garments for being worn on the lower torso of a wearer, said method comprising the steps of:
   (a) providing articles comprising at least one closed hoop structure, and at least a primary and a secondary web material; wherein manufacturing being performed on a high speed manufacturing equipment comprising:
      web supply means;
      a blank forming means;
      a means for cutting discrete elements of a web of blanks; and
      a means for transferring said blanks to a parallel treatment unit being a turret or an endless track, said parallel treatment unit comprising at least two web treatment sections for parallel treatment of said blanks;
      wherein each parallel treatment section comprising a treatment head, comprising:
         a centre plate, being positioned essentially parallel to the surface of said parallel treatment unit, to which said blanks are transferred;
         longitudinal extension plates positioned or extending forwardly and rearwardly of said centre plate along the overall manufacturing direction of said parallel treatment unit, and pivotable such that the forward or rearward ends can be turned downwardly away from said surface of said parallel treatment unit whilst the respective other ends of said extension plates remain adjacent to said centre plate; and
         web fixation means;
      wherein said parallel treatment unit further comprising connecting means for connecting portions of said blank to other portions of said blank;
   (b) preparing a pre-cursor blank comprising a centre piece comprising said primary web, said centre piece consisting of a centre region, and a front and a rear region extending longitudinally from said centre region, said pre-cursor blank further comprising side portions extending laterally outwardly of both sides of said centre region, said side portions comprising said secondary web, thusly forming a Plus-shaped precursor blank;
   (c) transferring said pre-cursor blank to said parallel treatment unit comprising said treatment sections, each treatment section comprising said treatment head;
   (d) temporarily attaching said centre region of said precursor blank to the surface of said centre plate of said treatment head which is out- or upwardly facing, and said front and rear regions to the longitudinal extension plates of said treatment head, whilst these are in an upwardly folded position essentially aligned with said centre plate;
   (e) separating said primary web into individual pieces, before or after having formed said precursor blank;
   (f) pivoting the outward front or rear ends of said longitudinal extension plates downwardly away from said surface of said parallel treatment unit whilst said front and rear regions of said blank remain attached thereto;
   (g) folding said side portions of said pre-cursor blank downwardly, so as to bring the side margins of said front and rear regions and the side margins of the side portions into an adjacent or overlapping positioning;
   (h) connecting respective side margins, thereby forming a closed article comprising a hoop;
   (i) optionally further treating the article; and
   (j) removing the article from the parallel treatment unit.

2. The method for manufacturing shaped articles according to claim 1, wherein said treatment unit further comprises side plates extending laterally outward of said centre plates of said treatment head, wherein said side plates are pivotably connected to said centre plate.

3. The method for manufacturing shaped articles according to claim 1, wherein the pivoting of said longitudinal and/or lateral extension plates is achieved by drive means selected from the group of mechanical drives being cam drives, pneumatic drives, electric drives, or servo drives.

4. The method for manufacturing shaped articles according to claim 1, wherein said centre plate and/or said longitudinal and/or lateral extension plates comprise a web fixation means being a vacuum suction means.

5. The method for manufacturing shaped articles according to claim 1, further comprising the step of (k) adding a further web material to said pre-cursor blank, wherein said further web material is essentially endless and connects the side portions of consecutive pre-cursor blanks by the laterally outward perimeter of said side portions.

6. The method for manufacturing shaped articles according to claim 5, wherein said further web material is separated into segments after said precursor blank has been transferred to said treatment head, and after said longitudinal extension plates with said front and rear region attached thereto have been downwardly folded, wherein the separating of said further material is executed essentially concurrently to connecting said cut edges to the front and rear regions, or together to form a closed hoop.

7. The method for manufacturing shaped articles according to claim 1, wherein in course of step (b) of forming said pre-cursor blank, said centre piece comprises cut lines, extending from the lateral outward perimeter inwardly, and wherein said side portions and said centre piece are connected by means of a connecting line or region essentially parallel and corresponding in cross-directional extension to said cut line.

8. The method for manufacturing shaped articles according to claim 1, wherein in course of step (b) of forming said pre-cursor blank a further material is added for forming a hoop with said side portion material.

9. The method for manufacturing shaped articles according to claim 1, wherein said step (f) is executed prior to step (g) so as to create an overlap connection of said front and rear regions with said side portions forming the leg/thigh panel, such that in this overlay connection the front and rear regions are positioned outwardly, relative to the wearer during use, of said leg/thigh panels.

* * * * *